United States Patent
Lopez et al.

(10) Patent No.: US 6,932,795 B2
(45) Date of Patent: Aug. 23, 2005

(54) POSITIVE FLOW VALVE

(75) Inventors: George A. Lopez, Laguna Beach, CA (US); Thomas F. Fangrow, Jr., Mission Viejo, CA (US); David C. Arnold, Mission Viejo, CA (US); Bruce M. Hubrecht, Canyon Lake, CA (US); Alison D. Brummett, Corona Del Mar, CA (US); Thomas J. Gustus, Costa Mesa, CA (US); Dennis M. Bui, Alta Loma, CA (US)

(73) Assignee: ICU Medical, Inc., San Clemente, CA (US)

( * ) Notice: Subject to any disclaimer, the term of this patent is extended or adjusted under 35 U.S.C. 154(b) by 104 days.

(21) Appl. No.: 10/163,719

(22) Filed: Jun. 5, 2002

(65) Prior Publication Data

US 2002/0147431 A1 Oct. 10, 2002

Related U.S. Application Data

(63) Continuation of application No. 09/411,988, filed on Oct. 4, 1999, now Pat. No. 6,428,520, which is a continuation of application No. 08/767,587, filed on Dec. 16, 1996, now abandoned.

(51) Int. Cl.$^7$ ............................................... A61M 5/00
(52) U.S. Cl. ..................... 604/249; 604/256; 604/246; 251/142
(58) Field of Search .............................. 251/142, 149.3, 251/149.7, 149.8, 4; 604/246, 30, 249, 256, 33, 28, 905, 533, 537

(56) References Cited

U.S. PATENT DOCUMENTS

| | | |
|---|---|---|
| 2,756,740 A | 7/1956 | Deane |
| 2,847,995 A | 8/1958 | Adams |
| 2,999,499 A | 9/1961 | Willet |
| 3,193,154 A | 7/1965 | Bross |
| 3,570,484 A * | 3/1971 | Steer et al. ................. 604/249 |
| 3,788,519 A | 1/1974 | Mengel |
| 3,831,629 A | 8/1974 | Mackal et al. |
| 3,965,910 A | 6/1976 | Fischer |

(Continued)

FOREIGN PATENT DOCUMENTS

| | | |
|---|---|---|
| CA | 2175021 | 11/1996 |
| CH | 670955 A5 | 7/1989 |

(Continued)

OTHER PUBLICATIONS

Excerpt from Braun's Memorandum of Points and Authorities in Support of its Motion for Summary Adjudication on the Priority Date of the '048 Patent.

(Continued)

*Primary Examiner*—Cris L. Rodriguez
(74) *Attorney, Agent, or Firm*—Knobbe Martens Olson & Bear LLP

(57) ABSTRACT

A closed system, spikeless, positive-flow valve device includes a body defining an internal cavity. At the proximal end of the body is an opening which is preferably sufficiently large to receive an ANSI standard tip of a medical implement. The valve includes a plastic, resilient silicon seal which fills the upper cavity and opening with an oval seal cap having a slit. The opening presses the oval seal cap to keep the slit closed in the decompressed state. The slit opens as the nose of the medical implement compresses the seal into the cavity and the seal cap is free from the opening. The housing also includes a fluid space which facilitates fluid flow between the medical implement and a catheter tip. The fluid space within the valve automatically and reversibly increases upon insertion of the medical implement into the cavity and decreases upon withdrawal of the medical implement, such that a positive flow from the valve toward the catheter tip is effected upon withdrawal of the medical implement, thereby preventing a flow of blood from a patient into the catheter when the medical implement is removed from the valve.

18 Claims, 18 Drawing Sheets

U.S. PATENT DOCUMENTS

| | | | |
|---|---|---|---|
| 3,986,508 A | | 10/1976 | Barrington |
| 4,243,034 A | | 1/1981 | Brandt |
| 4,306,705 A | | 12/1981 | Svensson |
| 4,334,551 A | | 6/1982 | Pfister |
| 4,512,766 A | | 4/1985 | Vailancourt |
| 4,610,469 A | | 9/1986 | Wolff-Mooij |
| 4,666,429 A | | 5/1987 | Stone |
| 4,804,015 A | | 2/1989 | Albinsson |
| 4,874,377 A | | 10/1989 | Newgard et al. |
| 4,915,687 A | | 4/1990 | Sivert |
| 4,917,668 A | | 4/1990 | Haindl |
| 5,006,114 A | | 4/1991 | Rogers et al. |
| 5,049,128 A | | 9/1991 | Duquette |
| 5,065,783 A | | 11/1991 | Ogle, II |
| 5,147,333 A | | 9/1992 | Raines |
| 5,154,703 A | | 10/1992 | Bonaldo |
| 5,163,922 A | | 11/1992 | McElveen, Jr. et al. |
| 5,201,717 A | | 4/1993 | Wyatt et al. |
| 5,203,775 A | | 4/1993 | Frank et al. |
| 5,221,271 A | | 6/1993 | Nicholson et al. |
| 5,242,432 A | | 9/1993 | DeFrank |
| 5,255,676 A | | 10/1993 | Russo |
| 5,269,771 A | | 12/1993 | Thomas et al. |
| 5,306,265 A | | 4/1994 | Ragazzi |
| 5,342,316 A | | 8/1994 | Wallace |
| 5,348,542 A | | 9/1994 | Ellis |
| 5,353,837 A | | 10/1994 | Faust |
| 5,380,306 A | | 1/1995 | Brinon |
| 5,401,245 A | | 3/1995 | Haining |
| 5,407,437 A | | 4/1995 | Heimreid |
| 5,417,673 A | | 5/1995 | Gordon |
| 5,439,451 A | * | 8/1995 | Collinson et al. ........... 604/247 |
| 5,470,319 A | | 11/1995 | Mayer |
| 5,509,433 A | | 4/1996 | Paradis |
| 5,520,665 A | | 5/1996 | Fleetwood |
| 5,535,771 A | * | 7/1996 | Purdy et al. ............. 137/15.01 |
| 5,549,566 A | | 8/1996 | Elias et al. |
| 5,549,651 A | | 8/1996 | Lynn |
| 5,555,908 A | * | 9/1996 | Edwards et al. ......... 137/329.1 |
| 5,569,235 A | | 10/1996 | Ross et al. |
| 5,578,059 A | * | 11/1996 | Patzer ........................ 604/249 |
| 5,603,706 A | | 2/1997 | Wyatt et al. |
| 5,620,434 A | * | 4/1997 | Brony ........................ 604/406 |
| 5,676,346 A | | 10/1997 | Leinsing |
| 5,699,821 A | | 12/1997 | Paradis |
| 5,730,418 A | | 3/1998 | Feith et al. |
| 5,749,861 A | | 5/1998 | Guala et al. |
| 5,882,348 A | | 3/1999 | Winterton et al. |
| 5,967,490 A | | 10/1999 | Pike |
| 5,979,868 A | | 11/1999 | Wu et al. |
| 6,009,902 A | | 1/2000 | Troiani et al. |
| 6,036,171 A | | 3/2000 | Weinheimer |
| 6,050,978 A | | 4/2000 | Orr et al. |
| 6,063,062 A | | 5/2000 | Paradis |
| 6,079,432 A | | 6/2000 | Paradis |
| 6,089,541 A | | 7/2000 | Weinheimer |
| 6,113,068 A | | 9/2000 | Ryan |
| 6,117,114 A | | 9/2000 | Paradis |
| 6,245,048 B1 | | 6/2001 | Fangrow, Jr. et al. |
| 6,428,520 B1 | | 8/2002 | Lopez et al. |

FOREIGN PATENT DOCUMENTS

| | | |
|---|---|---|
| EP | 263789 | 9/1987 |
| FR | 2439022 | 10/1979 |
| HU | P9902031 | 10/1999 |
| HU | P9902203 | 10/1999 |
| WO | WO 97/21463 | 6/1997 |
| WO | WO 97/21464 | 6/1997 |
| WO | WO 97/31676 | 9/1997 |
| WO | WO 98/26835 | 6/1998 |
| WO | WO 99/58186 | 11/1999 |

OTHER PUBLICATIONS

Ultrasite™ Systems "How It Works".

Capless Backcheck Valve.

F.D.A. 510(k) Summary of Safety and Effectiveness.

* cited by examiner

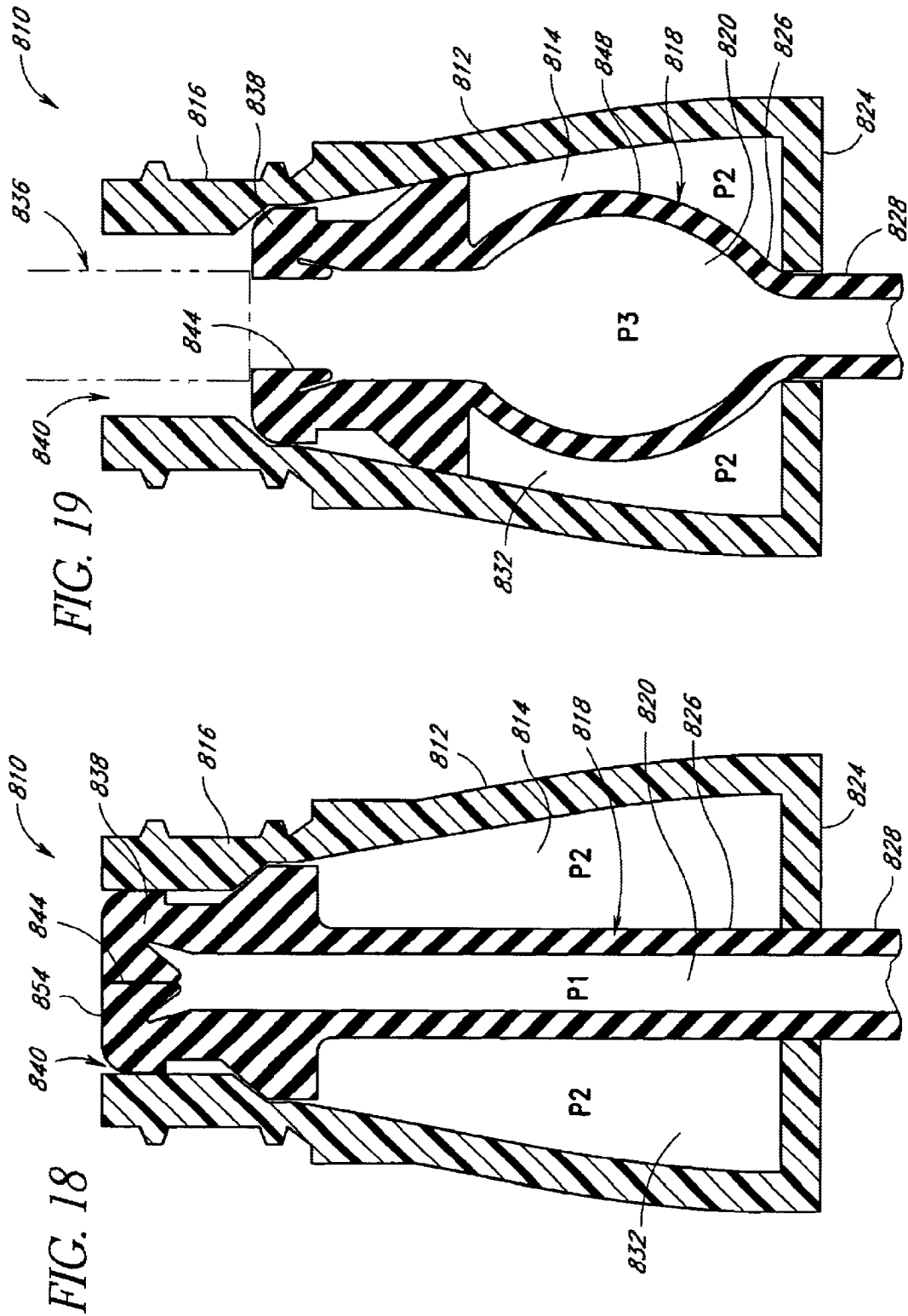

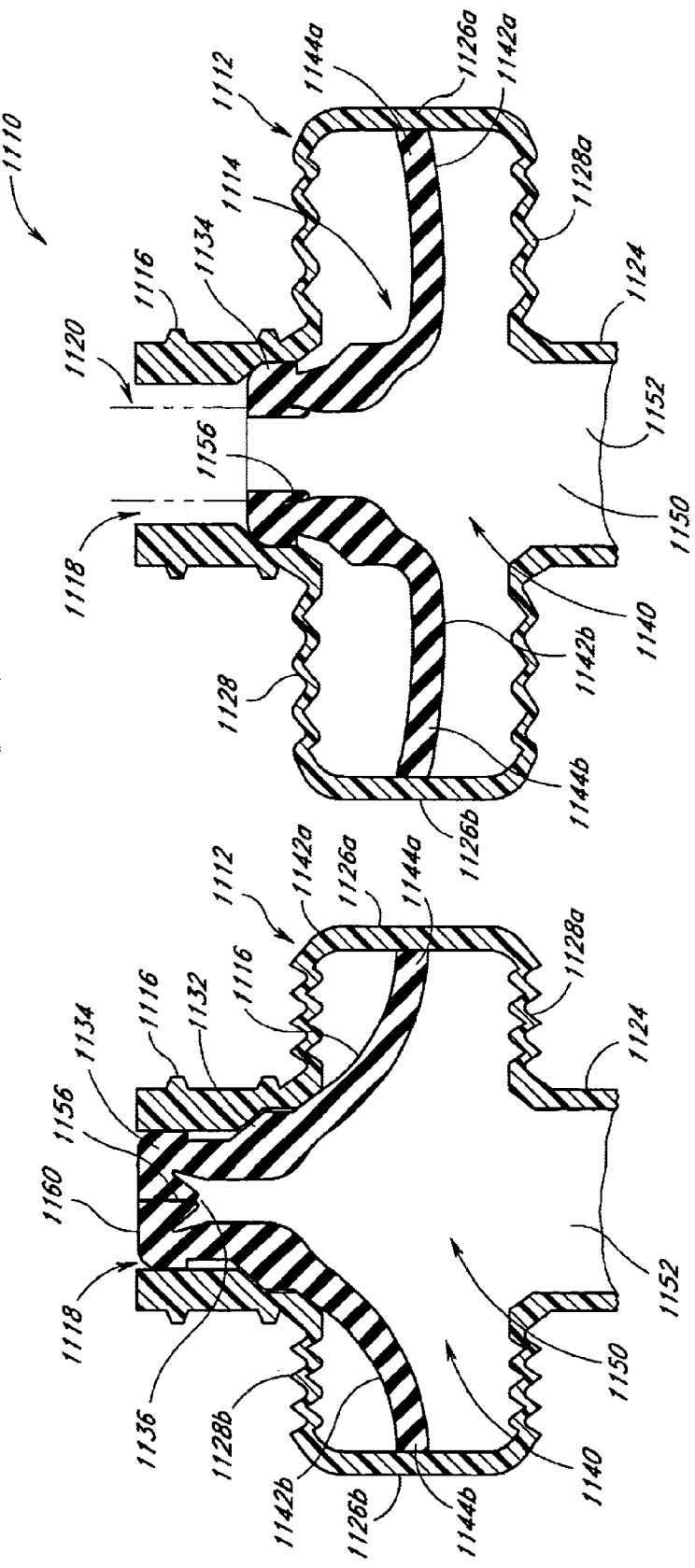

US 6,932,795 B2

POSITIVE FLOW VALVE

This application is a continuation of prior application Ser. No. 09/411,988 filed Oct. 4, 1999, now U.S. Pat. No. 6,428,520 which is a continuation of prior application Ser. No. 08/767,587, filed Dec. 16, 1996, now abandoned.

BACKGROUND OF THE INVENTION

1. Field of the Invention

This invention relates generally to a medical valve, and in particular to a positive flow valve which, when connected between a medical implement and a catheter to facilitate fluid flow therethrough, induces a positive flow of fluid through a tip of the catheter from the valve upon disconnection of the medical implement, thereby eliminating the problem of blood-clogging or clotting in the catheter.

2. Description of the Related Art

The manipulation of fluids for parenteral administration in hospitals and medical settings routinely involves the use of connectors and valves for facilitating the movement of fluids between two points. Fluid connectors and valves typically employ needles or luers to pierce a septum or seal covering sterile tubing or to pierce a septum or seal of a medicament container of fluid. Fluid then passes from the container or fluid-filled tubing into a syringe or second set of tubing. Since the ready passage of fluids through the connectors and valves is often critical to patient survival, it is imperative that the connectors and valves function reliably and repeatedly. Connectors and valves that malfunction during use may be life-threatening.

Many connectors or valves, especially those employing several mechanical components, have a relatively high volume of fluid space within them. There is potential for the creation of a "dead space" (i.e. an increase in the fluid containment area which will cause fluid within the patient to be drawn therein) in the fluid space during removal or disconnection of the tubing or other medical implements such as conduits, syringes, IV sets (both peripheral and central lines), piggyback lines, and similar components which can be used in connection with a medical valve. Withdrawal of the medical implement creates a suction force which draws fluid back toward the valve in a phenomenon known as "backflash." This is particularly troublesome in the case where the valve is connected through a catheter to a patient. A suction force is generated by the withdrawal of the medical implement which draws blood from the patient into the catheter. This blood clot and clog the catheter near its tip, rendering it inoperable, and may even result in a clot of blood in the patient, which may prove fatal. Attempts to avoid backflash by coating the inner surface of the catheter near its tip in order to prevent blood from sticking to the interior surfaces of the catheter and clogging it have not been successful.

The risk of blood clogging of the catheter is significantly heightened where the inner diameter of the catheter is small (e.g., 27 gauge). These small catheters have the advantage, however, that they reduce the trauma and discomfort caused by insertion into a patient. Because these catheters have a very small passage therethrough, even a small suction force may draw sufficient amount of fluid back through a catheter toward the valve to introduce blood into the catheter tip, which blood may clog the catheter's passage. This back flow is hereinafter referred to as a negative flow. FIG. 1 shows an example of a catheter 50 having a small portion near the tip 52 that is inserted into the patient, and a valve 54 connected between one end of the catheter and a medical implement 56. The problem associated with the creation of "dead space" or a drawing of fluid from the catheter towards the valve is illustrated by this Figure. As illustrated therein, when the tip or nose of the medical implement 56 is withdrawn from the valve 54, the space previously occupied by the implement 56 becomes "dead space." This newly created space has a lower pressure than the fluid within the valve, catheter and patient, such that fluid is drawn into that space, and thus travels from the patient in the direction of the dead space. To avoid blood from being drawn into the catheter, a zero flow or a positive flow, defined as flow or fluid displacement directed from the valve through the catheter tip to the patient, must be effected at the time the medical implement is withdrawn. For a sufficient margin of safety, a positive flow toward the patient is desirable.

To avoid negative flow or backflash, healthcare workers presently practice the method of disconnecting the valve and simultaneously transferring fluid through the catheter by manipulating the medical implement to induce positive flow. This method is clumsy and difficult, and may result in an inaccurate transfer of medicament.

One way to induce a positive flow in the catheter is illustrated in FIGS. 2a and 2b. Here, the proximal end of a valve 180 is enclosed with a stylet or displacer 182 upon withdrawal of the medical implement (not shown). An elongated portion 184 of the stylet 182 takes up at least a portion of the fluid space, thereby reducing the volume of the fluid space, and may eliminate the dead space therein. The elongated portion 184, however, must be sufficiently long to displace more fluid than that volume of fluid which may be drawn from the catheter towards the valve by the withdrawal of the implement, and hence may be difficult to construct for proper performance. The use of the stylet 182 further requires an additional step that may be overlooked by the nurse and the stylet 182 may be misplaced or lost. In addition, this specific type of valve 180 has many significant drawbacks, among them the fact that it does not have a seal with a swabbable surface that can be swabbed after each use for sterility.

SUMMARY OF THE INVENTION

In accordance with the present invention there is provided a positive flow valve which is advantageously utilized between a catheter and another medical implement, and with which the flow of a fluid between the implement and catheter (and a patient within which the catheter is employed). The valve of this invention has several features, no single one of which is solely responsible for its desirable attributes.

In general, the positive flow valve of the present invention has the attributes of safety, positive flow for eliminating dead space, reliable and repeatable performance, simplicity of manufacture and use, a seal for use in establishing fluid flow which need not be pierced with a sharp spike or cannula, suitability of high pressure applications, and employment of a valve that is swabbable after use to provide sterility and has a fluid-tight seal at high pressure.

The present invention is a swabbable, needle-less, positive flow valve that has a fluid space which automatically expands upon insertion of a medical implement and contracts upon withdrawal of the medical implement. When the valve is connected to a catheter, it induces a positive flow from the valve to the catheter tip upon disconnection of the medical implement to avoid the potential problems of blood-clogging. After use, the valve is swabbed in the conventional manner with a suitable substance to maintain sterility. The design of the valve avoids accidental needle or spike sticks.

The valve is particularly suited for applications with a catheter where it is desirable to avoid backflash, but may be used for other applications as well.

Preferably, the valve includes a housing having a first end adapted for receiving one end of medical implement, and having a second end in communication with a catheter. The valve includes means for establishing a fluid flow path through the housing and between the medical implement and the catheter, and which is also useful in occluding the flow path through the housing and thereby preventing fluid flow between the medical implement and catheter.

Preferably, this means comprises a seal movably positioned within the housing. The seal has a passage therethrough which defines, in at least one area, a fluid containment area. The seal has a first end adapted for engagement by the medical implement. In a first position, the passage through the seal is closed at its first end, and in a second position, when the medical implement is utilized to press the seal distally within the housing of the valve, the passage through the valve is opened.

Most importantly, when the medical implement is utilized to press the seal distally and establish fluid flow therethrough, the fluid containment area therein increases in total volume, thereby retaining a fluid volume therein. When the medical implement is retracted from the valve, the seal returns to its position wherein the passage is closed at the proximal end thereof, and the volume of the fluid containment area is reduced. This reduction in fluid containment volume results in a volume of fluid being forced towards the catheter (i.e. a positive flow is established).

BRIEF DESCRIPTION OF THE DRAWINGS

The preferred embodiments of this invention, illustrating all its features, will now be discussed in detail. These embodiments depict the novel and nonobvious method and valve of this invention shown in the accompanying drawings, which are for illustrative purposes only. The drawings include the following Figures, with like numerals indicating like parts:

FIG. 18 is a longitudinal cross-sectional view of the eighth embodiment of the positive-flow valve of this invention before compressing the seal.

FIG. 19 is a longitudinal cross-sectional view similar to FIG. 18 showing the valve during compression of the seal.

FIG. 24 is a longitudinal cross-sectional view of the eleventh embodiment of the positive-flow valve of this invention before compressing the seal.

FIG. 25 is a longitudinal cross-sectional view similar to FIG. 24 showing the valve during compression of the seal.

DETAILED DESCRIPTION OF THE PREFERRED EMBODIMENT

Figure 3:
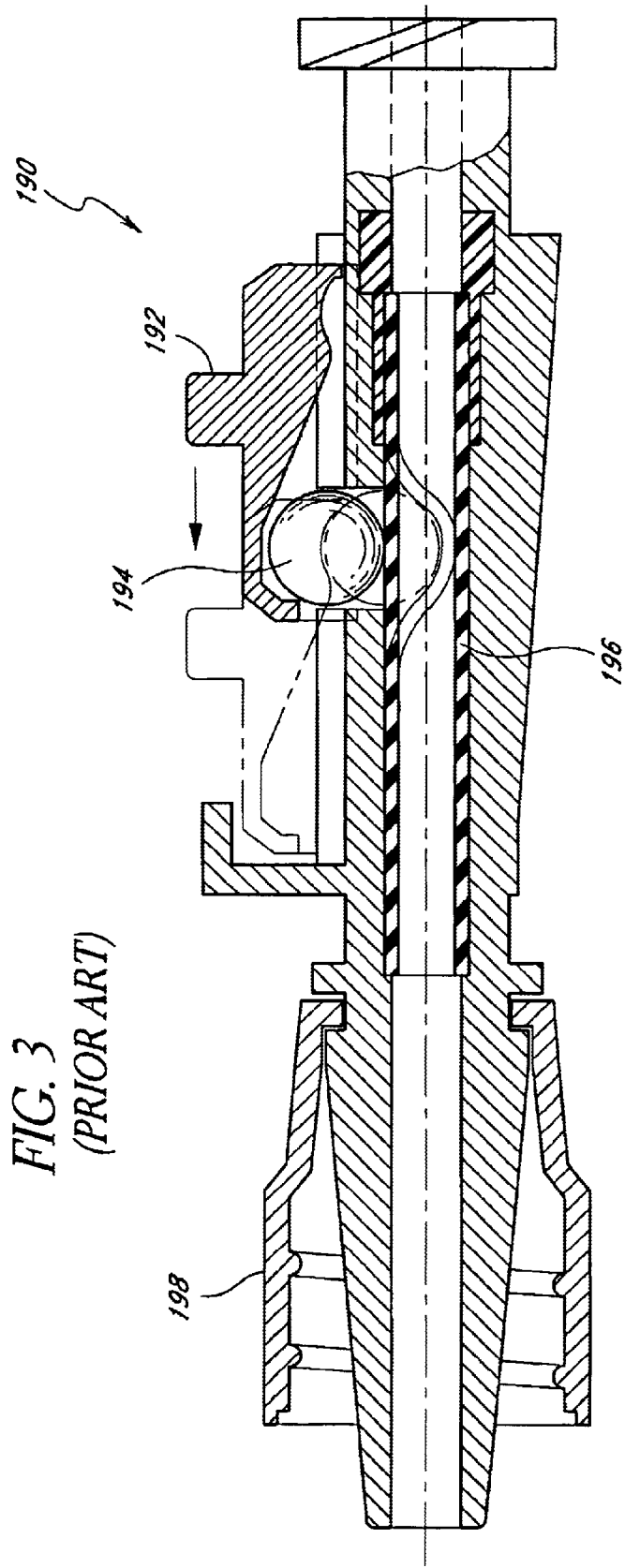
FIG. 3 is a schematic cross-sectional view of a roller-clamp valve which may be manually activated to induce a positive flow through a catheter tip from the valve.

The Applicant has recognized that a roller clamp may be used to induce a positive flow in a medical valve. The use of a roller clamp in a medical valve 190 to create a positive flow upon disconnection of a medical implement (not shown) is illustrated in FIG. 3. The roller-clamp valve 190 is activated manually by sliding an external switch 192 to push a roller 194 against tubing 196 which connects a medical implement 198 and a catheter (not shown) to cause a positive pressure therein, thereby creating a positive flow through the catheter tip (not shown). The flow through the tubing 196 can be opened by sliding the switch 192 in the reverse direction.

Figure 1:
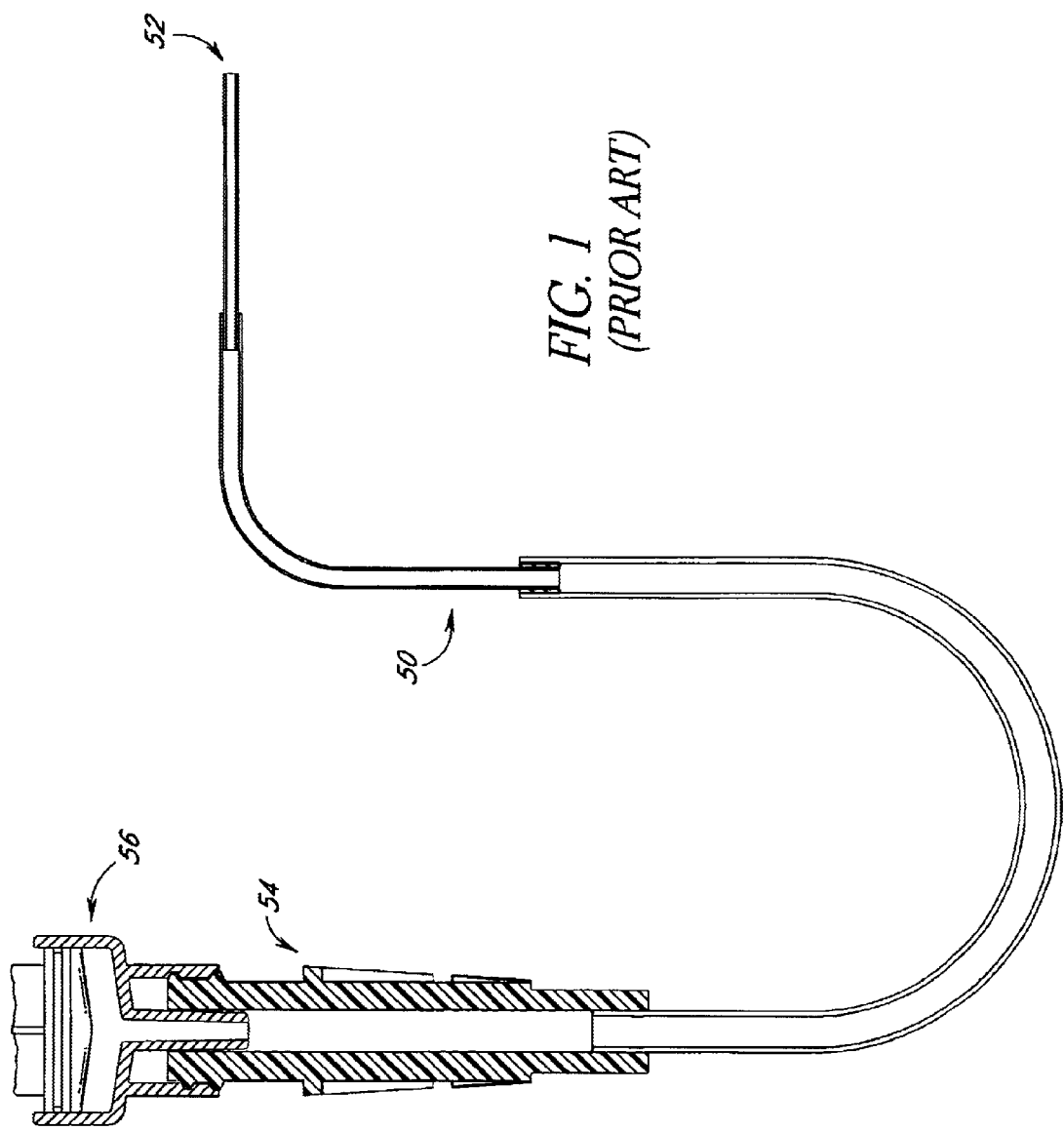
FIG. 1 is a schematic cross-sectional view of a valve forming a fluid connection between a syringe and a catheter.
Figure 2:
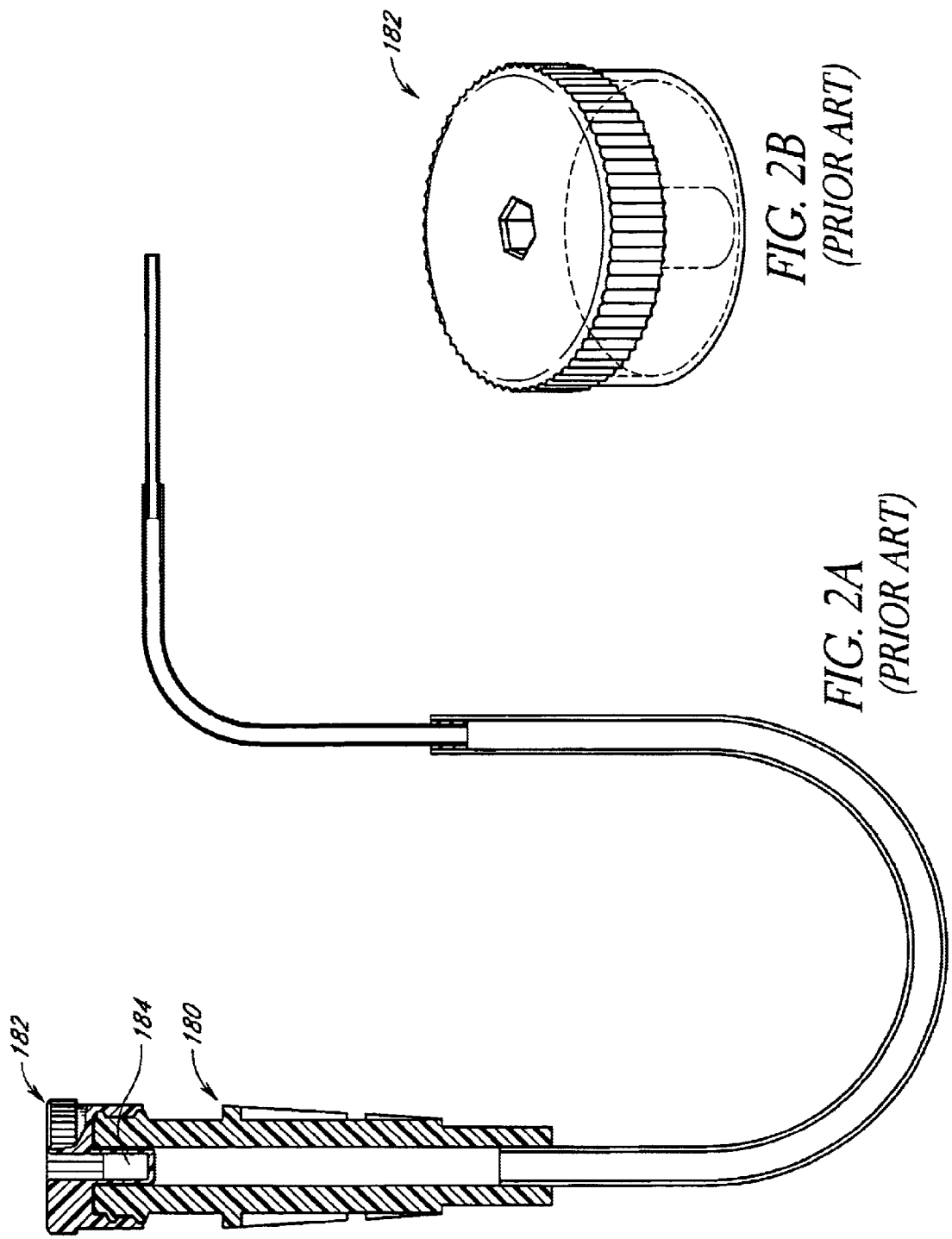
FIGS. 2a and 2b illustrate a prior art valve which includes a stylet having an elongated portion after use to induce a positive flow.

This valve 190, however, has the same disadvantage of requiring an additional step of operation as does the valve with a stylet illustrated in FIGS. 2a and 2b, and also does not include a seal having a swabbable surface. Furthermore, the size of the roller 194 must be sufficiently large to induce a displacement of fluid within the tube which is greater than the amount of fluid which may be drawn by the vacuum force (so as to generate a positive flow), which may require a bulky valve that is hard to operate.

First Embodiment

Figure 4:
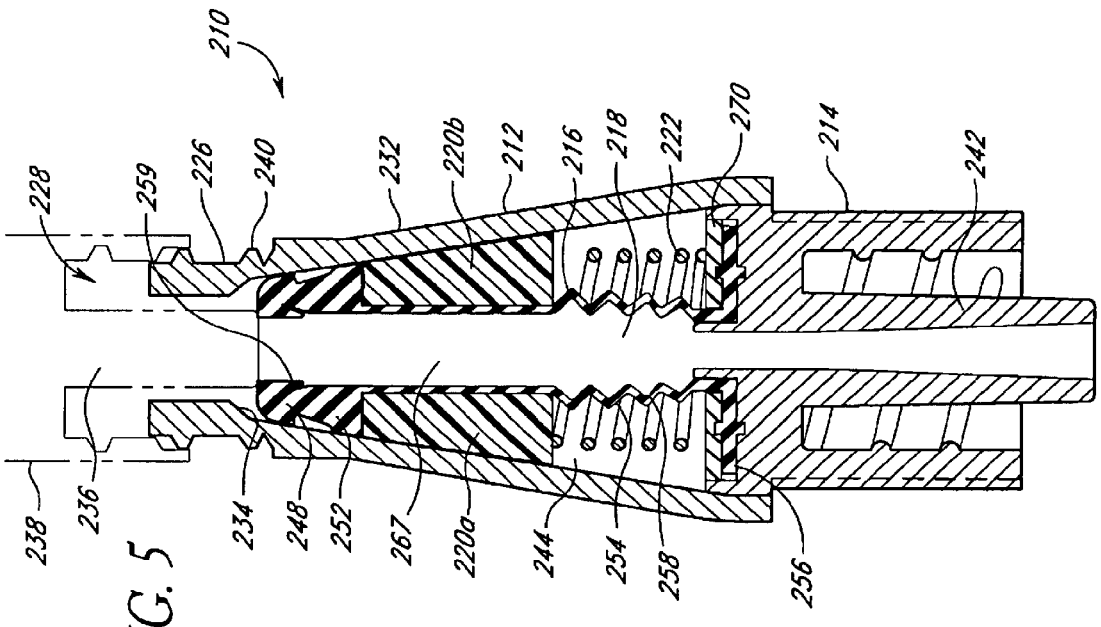
FIG. 4 is a longitudinal cross-sectional view of the first embodiment of the positive-flow valve of this invention before compressing the seal.
Figure 5:
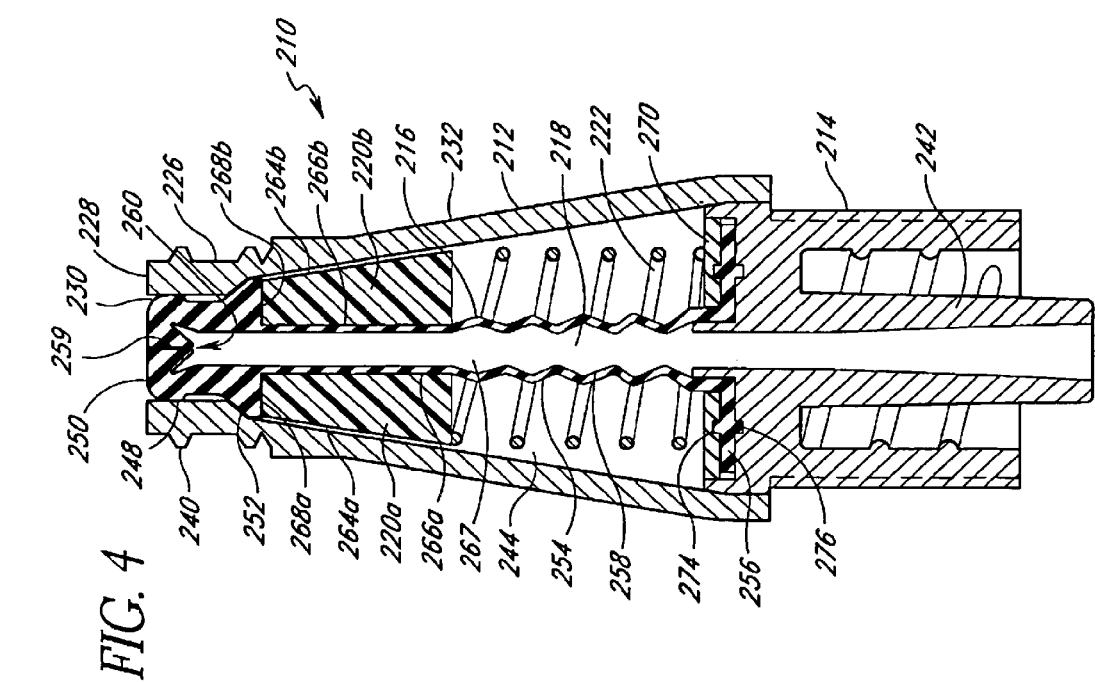
FIG. 5 is a longitudinal cross-sectional view similar to FIG. 4 showing the valve during compression of the seal.

FIGS. 4 and 5 illustrate a first embodiment of a valve 210 in accordance with the present invention. In general, this valve 210 includes a valve body or housing 212, a support member 214, a seal 216 defining an inner cavity 218, a pair of clam shells 220a and 220b, and a spring 222. These components are assembled, as depicted in FIG. 4, without the need for a spike element. The inner cavity 218 forms an expandable fluid space inside the valve 210. As discussed below, the clam shells 220a/220b are constructed to cause the volume of the fluid space to expand or increase upon insertion of a medical implement and to contract or decrease upon withdrawal of the medical implement.

The body or housing 212 has an upper conduit 226 near a proximal end 228, desirably with a circular opening 230 that is adapted to receive the medical implement. A side wall portion 232 is preferably tapered to cooperate with the clam shells 220a/220b. The body 212 has an upper ledge 234 formed between the proximal end 228 and the side wall portion 232. There is desirably a threaded portion on the housing 212 adjacent the circular opening 230 in the top of the upper conduit 226, as best seen in FIG. 4. Note that "proximal" is used to denote the end of the valve 210 and other components at or near the body opening 230, while "distal" is used to denote the opposite end of the valve.

In the first embodiment, the upper conduit 226 is adapted to receive the tip or nose 236 of an ANSI standard syringe 238, as shown in phantom in FIG. 5. It is, however, contemplated that the outer diameter of the upper conduit 226 can be of any size to accommodate the attachment of other connector devices thereto. Advantageously, the proximal end of the upper conduit 226 can be equipped with a locking mechanism to facilitate locking of the valve 210 to a variety of connector devices. For example, referring to FIG. 4, the threaded portion of the housing 212 are preferably provided such that the housing 212 can be locked into any compatible Luer-Lock device known to those with skill in the art. The housing 212 of the first embodiment according to this invention includes conventional Luer-Lock threads 240 on the outer diameter of the upper conduit 226.

The support member 214 has at its distal end the inner conduit 242 which may be connected to a terminal end of a catheter (not shown). The support member 214 serves as a support and attachment device for the seal 216 by holding the seal 216 in place inside the internal cavity 244 of the housing 212. The inner conduit 242 and inner cavity 218 of the seal 216 present a continuous passageway for fluid during use.

The seal 216 is prepared from a resilient material that is flexible, inert, and impermeable to fluid, such as silicon. The seal 216 has a seal cap 248 with a generally flat top surface 250, a shoulder 252, a side wall 254, and a base 256. The side wall 254 advantageously is comprised of wall portions 258 which deform in an accordion-like fashion and assist in the reformation of the seal 216 to close the housing opening 230 upon withdrawal of the syringe 238. During compression of the seal 216, the wall portions 258 expand outwardly in the radial direction. The interior of the seal 216 is hollow to provide the inner cavity 218, as best seen in FIG. 4. There are preferably gaps between the wall portions 258 which facilitate deformation and reformation of the seal 216. The shoulder 252 engages the upper ledge 234 provided in the upper conduit 226 of the housing 212 such that the upper ledge 234 confines the movement of the shoulder 252 toward the opening 230 to prevent the seal 216 from being blown through the opening 230 under high pressure in the inner cavity 218 of the seal 216.

The seal cap 248 reseals the valve 210 at the opening 230, with the top surface 250 of the seal 216 approximately flush with or slightly above or below the opening 230 upon removal of the medical implement 238. Preferably, the seal cap 248 substantially fills the opening 230 in the top of the upper conduit 226. After assembly, the top surface 250 of the seal cap 248 is essentially flush with the opening 230, so that the seal cap 248 can be swabbed with alcohol or other disinfectant without leakage of the disinfectant into the valve 210. Therefore, it is preferable that the top surface 250 be exposed so that it may be swabbed with a disinfectant.

To provide a fluid-tight seal at the opening 230 and to eliminate the need for a spike element to induce fluid flow upon insertion of a medical implement, the seal cap 248 has a unique shape and includes a precut slit 259, also having a unique shape. The seal cap 248 desirably has an oval or elliptical shape with a major axis having a length larger than the inner diameter of the circular opening 230 such that the oval seal cap 248 substantially fills the opening 230 in the top of the upper conduit 226 in the decompressed state. The precut slit 259 in the seal cap 248 is squeezed shut by the circular opening 230 in the decompressed state, as seen in FIG. 4. In its resting state, the precut slit 259 is open. During compression of the seal 216 by insertion of a medical implement such as the syringe 238, as illustrated in FIG. 5, the precut slit 259 returns to its resting state and opens, as the seal cap 248 is allowed to stretch in the portion of the upper conduit 226 which has a larger inner diameter. Fluid is thus allowed to pass through the slit 259. Note that the terms "compressed state" and "decompressed state" are used conveniently to refer to compression and decompression of the seal 216 by insertion and withdrawal of the medical implement 238 along the longitudinal axis of the seal 216. The terms do not relate to the radial compression of the seal cap 248 by the opening 230 of the housing 212.

To further assist in creating a fluid-tight seal in the decompressed state, the seal 216 of FIG. 4 advantageously includes the enlarged, internal, pressure responsive member 260 which is integral with the seal cap 248. The pressure responsive member 260 enables the valve 210 to maintain a fluid-tight seal even at very high pressures sometimes experienced in medical applications, particularly when the valve 210 is connected to a patient's artery.

As shown in FIGS. 4 and 5, the clam shells 220a/220b are desirably identical pieces disposed opposite one another symmetrically inside the valve body 212. They are preferably made of a firm material such as a hard plastic. The external surface 264a/264b of each clam shell 220a/220b is tapered to cooperate with the tapered side wall portion 232 of the housing 212, and is configured to slide along the side wall portion 232 during compression and decompression.

The internal surfaces 266a/266b of the clam shells 220a/220b cooperate with one another to squeeze a portion of the seal side wall 254, preferably adjacent the shoulder 252, to form a constricted portion 267 of the seal 216. The proximal ends 268a/268b of the clam shells 220a/220b engage the shoulder 252 of the seal 216 to facilitate movement of the clam shells 220a/220b with the compression of the seal 216. The internal surfaces 266a/266b preferably are shaped to cause the constricted portion 267 to be substantially circular. In this embodiment, each internal surface 266a/266b has a semi-circular, longitudinal groove that squeezes the seal 216.

The spring 222 is disposed between the distal ends of the clam shells 220a/220b and the base 256 of the seal 216, but desirably a hard retaining disk 270 is provided adjacent the base 256 of the seal 216 to provide better support for the spring 222 and the seal 216. In the decompressed state shown in FIG. 4, the spring 222 may be relaxed or be in slight compression to exert a force on the seal 216 through the clam shells 220a/220b to keep the seal 216 closed. During insertion of the syringe 238, the spring 222 is compressed and stores potential energy from the compression, as illustrated in FIG. 5. Upon withdrawal of the syringe 238, the spring 222 releases the potential energy and pushes the clam shells 220a/220b proximally to close the seal 216, as shown in FIG. 4. The spring 222 is preferably not attached or bonded to either the clam shells 220a/220b or the retaining disk 270 for ease of assembly. Although FIGS. 4–5 show a helical spring 222, any suitable spring known to those of skill in the art may be used.

The seal 216 is desirably relaxed longitudinally in the decompressed state (FIG. 4), and compressed longitudinally in the compressed state (FIG. 5). Alternatively, the seal 216 may be stretched longitudinally in tension by the spring 222 in the decompressed state and be relaxed or slightly compressed longitudinal in the compressed state. The base 256 of the seal 216 advantageously fits snugly and securely into a annular groove 274 provided in the retaining disk 270 and an annular groove 276 provided in the support member 214. The annular grooves 274,276 form a locking mechanism to support and secure the seal 216 within the cavity 244 of the housing 212.

To illustrate valve activation, FIG. 5 shows the compressed state of the valve 210 upon insertion of the syringe 238. A medical implement other than a syringe as known to those of skill in the art may be used. The nose 236 of the syringe 238 is placed on the seal cap 248 inside the opening 230 of the housing 212. The application of pressure on the syringe 238 creates pressure on the seal cap 248, and the resulting downward pressure compresses the seal 216. This pushes the seal cap 248 away from the circular opening 230 and toward the lower portion of the housing cavity 244 which has a larger inner diameter, thereby allowing the precut slit 259 to open. The downward movement is facilitated by the compression of the spring 222 which stores the potential energy of compression and by the gaps between the wall portions 258 of the side wall 254 of the seal 216. Fluid is now able to flow into the syringe 238, or vice versa, depending on whether fluid is to be withdrawn from the patient or medication injected into the patient. FIG. 5 shows the valve 210 opened by insertion of the nose 236 of the syringe 238 into the opening 230. For intravenous applications, the valve 210 can be oriented in the position diagramed in FIGS. 4 and 5, or it can be rotated 180' such that fluid flows in the opposite direction.

In the compressed state shown in FIG. 5, the inner cavity 218 of the seal 216 generally contracts (becomes shorter) as compared to the decompressed state shown in FIG. 4. The constricted portion 267 of the inner cavity 218, defined by the clam shells 220a/220b, however, expands (becomes larger) in volume when the seal 216 is in the compressed state. This results from a movement of the clam shells 220a/220b apart from one another as they slide along the tapered side wall 232 of the housing 212. The amount of general contraction of the seal 216 in relation to the amount of expansion of the constricted portion 267 during compression determine whether the valve 210 generates a positive, negative, or zero flow upon decompression, as discussed below.

Upon removal of the syringe 238 from the upper conduit 226, as shown in FIG. 4, the seal 216 is free to move toward its decompressed state, and the clam shells 220a/220b are pushed proximally toward the opening 230. The movement causes a general expansion of the inner cavity 218 (i.e., the cavity increases in length), but causes a contraction (i.e., reduction in size) of the volume of the constricted portion 267 of the seal 216. If the volume change associated with the contraction of the constricted portion 267 equals the volume change associated with the expansion of the inner cavity 218, the fluid space or inner cavity will have zero flow. If the increase in volume associated with the expansion of the inner cavity 218 is greater than the reduction in volume associated with the contraction of the constricted portion 267, there will be a net gain in fluid space, resulting in an undesirable negative flow toward the valve 210 through, e.g., a catheter tip (not shown). If the reduction in volume associated with the contraction of the constricted portion 267 is greater than the increase in volume associated with the expansion of the inner cavity 218, there will be a desirable positive flow from the valve 210 through the catheter tip (not shown). Thus, for the valve 210 to be a positive-flow valve requires that the clam shells be configured to allow greater expansion of the constricted portion 267 (i.e., an increase in fluid volume in that area of the seal 216) than the general contraction volume change associated with the expansion of the inner cavity 218 of the seal 216 upon compression and, hence, greater contraction (i.e., decrease in fluid volume within that area of the seal) of the constricted portion 267 than the general expansion (i.e., increase in fluid volume in that area of the seal) of the seal 216 upon decompression. In other words, for the valve 210 to induce positive flow upon disconnection of the medical implement 238 therefrom, the total fluid volume within the valve 210 must decrease. In the instant case, this decrease in fluid volume is effectuated by causing the fluid volume within the seal to decrease as between its compressed (when syringe attached) and uncompressed (when syringe detached) states. This reduction or decrease in available fluid volume within the valve 210 causes fluid to flow towards the catheter/patient, preventing blood from being drawn into the catheter.

That the valve 210 is advantageously configured to be a positive-flow valve 210 eliminates any dead space during decompression of the seal 210 as the syringe 238 is withdrawn, as illustrated in FIG. 4. Furthermore, as the syringe 238 is withdrawn, the slit 259 remains open until the very end, i.e., until the seal cap 248 is squeezed by the circular opening 230 at the top of the upper conduit 226. This further assists in eliminating dead space and avoiding backflash. This feature is particularly advantageous in the case where the valve 210 is connected through a catheter to a patient, because it prevents blood from being drawn into the catheter and clogging it. This invention therefore eliminates a significant risk by solving the problem of backflash.

As the seal 216 is free to move to its decompressed state, it essentially fills the opening 230. The ability of the seal 216 to return to its original shape and be deformed in its decompressed state is determined by the resiliency of the material used to prepare the seal 216. Advantageously, the ability of the seal 216 to return to its decompressed state is facilitated by the spring 222 and the gaps between the wall portions 258 of the seal 216. The ability of the seal 216 to deform reversibly and return to its decompressed state is particularly useful because (1) it immediately stops fluid flow through the valve 210, and (2) it maintains sterility of the valve.

The ability of the seal 216 to return reversibly to its decompressed state permits reuse of the valve 210. Following disconnection, and before reuse, the surface 250 of the seal cap 248 is essentially flush with the opening 230 of the housing 212. Thus, this flush surface 250 can advantageously be sterilized with alcohol or other surface-decontaminating substances. The support member 214 and body 212 advantageously shield both connections from the surrounding environment to protect the sterility of the connection.

A cover cap (not shown) can be supplied to fit over the upper conduit 226 as further protection for the surface 250 of the seal cap 248 when not in use. Such a cover cap, however, is not needed to maintain sterility since the seal 216 may be swabbed with a disinfectant before and/or after each use. Reversibility of the seal 216 makes the valve 210 particularly attractive as a connector valve to provide fluid communication between two fluid lines. Therefore, the present invention provides for placing a first fluid line in communication with a second fluid line using the valve 210 disclosed herein. The reversibility of the valve 210 permits multiple fluid lines to be successively added, for example, to a fluid line in direct communication with a patient's vein. Since the valve 210 is easily sterilized and sealable, fluid lines can be added and removed without disconnecting venous contact of the catheter.

The valve body 212 and support member 214 are preferably prepared from a hard plastic, but it is additionally contemplated that the valve 210 could be prepared from other medically inert materials known to those skilled in the art. Another feature of this invention is that it relies neither on a needle nor on a spike in order to establish fluid flow through the valve. This completely eliminates the risk of skin puncture or fear of puncture during use and manufacture. It also eliminates coring of the seal 216 by a spike element and all the risks associated therewith. Further, the fluid flow rate is not limited by the size of a through passage in a needle or spike, as is the case in some prior art valves.

As shown in FIG. 4, another feature of the invention is that the upper ledge 234 confines the movement of the shoulder 252 toward the opening 250 to prevent the seal 216 from being blown through the opening 230 under high pressure in the cavity 218. This makes the valve 210 particularly suited for high pressure applications.

Second Embodiment

Figure 6:
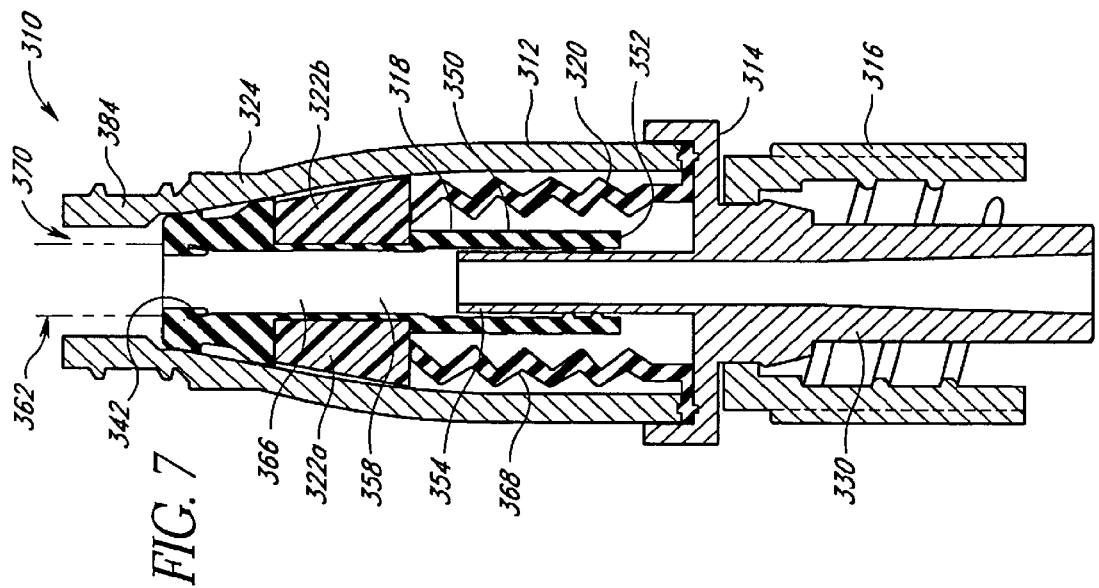
FIG. 6 is a longitudinal cross-sectional view of the second embodiment of the positive-flow valve of this invention before compressing the seal.
Figure 7:
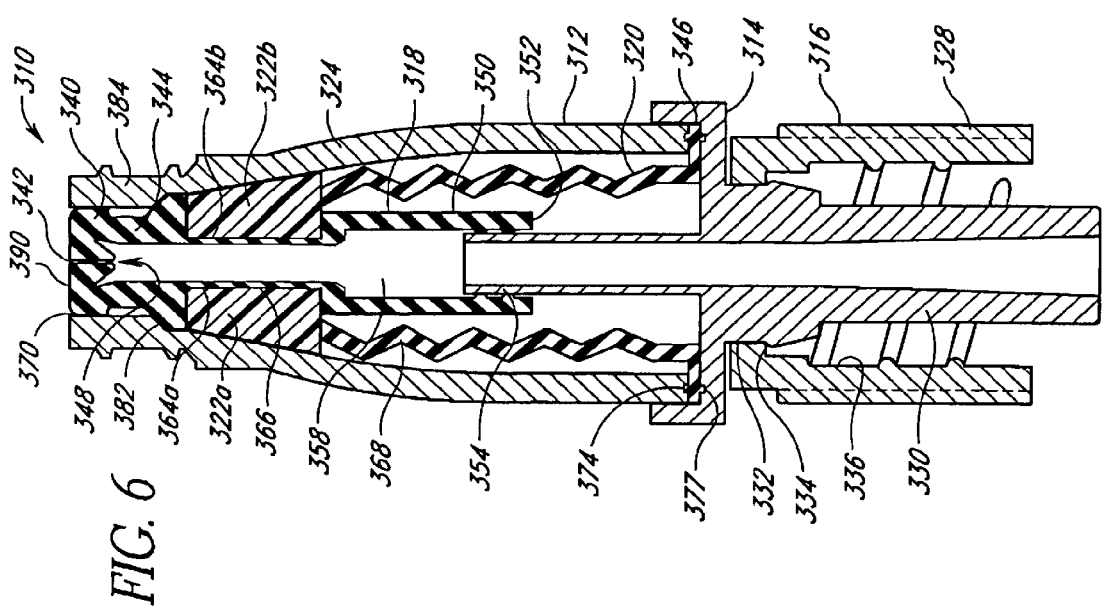
FIG. 7 is a longitudinal cross-sectional view similar to FIG. 6 showing the valve during compression of the seal.

In a second embodiment of the present invention illustrated in FIGS. 6 and 7, the valve 310 includes a valve body or housing 312, a support member 314, a skirt 316, a seal 318, a resilient member 320, and a pair of clam shells 322a/322b. The housing 312 is desirably similar to the housing 212 of FIG. 4 and has a tapered side wall 324.

Referring to FIGS. 6 and 7, the second embodiment of the valve 310 has a bell-shaped skirt 316. The skirt 316 has an annular ring 328 which is disposed toward an inner conduit 330 of the support member 314. The skirt 316 creates a shield for the inner conduit 330. This inner conduit 330 is preferably cylindrical in shape and slightly tapered. The inner conduit may be connected to a terminal end of a catheter (not shown), which has an opposite, open end that is generally inserted into a patient. The support member 314 serves as a support and attachment device for the seal 318 by holding the seal 318 in place inside the housing 312.

The support member 314 also serves as a support and attachment device for the skirt 316. As best seen in FIG. 6, the support member 314 has an edge portion 332 which engages a ledge 334 of the skirt 316 in assembly. This attachment secures the skirt 316 in place. The skirt 316 desirably includes a Luer-Lock portion 336 that enables the valve 310 to be removably attached to, for example, a fluid line or catheter connected to a patient. It is noted that the valve 310 in this embodiment includes a skirt 316 separate from the housing 312 for ease of assembly. A different embodiment can provide a unitary member which replaces the housing 312 and skirt 316. It is therefore contemplated that such an embodiment would fall within the scope of this invention.

The seal 318 is similar to the seal 210 of FIG. 4. The seal 318 is also preferably silicon and has a similar seal cap 340 with a precut slit 342, shoulder 344, and pressure responsive member 348. These components serve the same function as those of the seal 210. Instead of a side wall formed with wall portions 258, the seal 318 has a side wall 350 that is generally circular cylindrical and has a distal portion 352 that is sized to be slip-fitted with the proximal end 354 of the inner conduit 330 of the support member 314. During compression of the seal 318, the side wall 350 simply slides over the proximal end 354 of the inner conduit 330, forming a fluid-tight seal therewith. The seal 318 defines an inner cavity 358 above the proximal end 354 of the inner conduit 330. The inner cavity 358 forms an expandable fluid space inside the valve 310. The inner conduit 330 and inner cavity 358 comprise aligned hollow tubes in fluid communication with each other when the precut slit 342 of the seal 318 opens during compression of the seal 310.

Similar in form and function to the clam shells 220a/220b of FIGS. 4 and 5, the clam shells 322a/322b are constructed to cause an increase in fluid space upon insertion of a medical implement into the valve 310 and a decrease in fluid space upon withdrawal of the medical implement such as a syringe 362 partially shown in phantom in FIG. 7. The internal surfaces 364a/364b of the clam shells desirably have longitudinal grooves that cooperate with one another to squeeze a portion of the seal side wall 350 to form a constricted portion 366 thereof.

Instead of the spring 222 in FIG. 4, the second embodiment employs the resilient member 320 disposed between the clam shells 322a/322b and the support member 314. The resilient member 320 advantageously is inert and impermeable to fluid such as silicon, and includes wall portions 368 which deform in an accordion-like fashion and assist in the reformation of the seal 318 to close the housing opening 370 upon withdrawal of the syringe 362. The resilient member 320 thus is similar in construction with and serves the same function as the spring 222 of the seal 210 of FIGS. 4 and 5. It is contemplated that a spring (not shown) similar to the spring 222 of FIG. 4 may be used in place of the resilient member 320, as may other suitable structures known to those of skill in the art.

As shown in FIGS. 6 and 7, the resilient member 320 has a base 346. The base 346 fits snugly and securely within an annular groove 374 provided in the housing 312 and an annular groove 377 provided in the support member 314, as shown in FIG. 6. The annular grooves 376,377 hence form a locking mechanism to support and secure the resilient member 320 within the housing 312. The shoulder 344 engages an upper ledge 382 provided in an upper conduit 384 of the housing 312 such that the upper ledge 382 confines the movement of the shoulder 344 toward the opening 370 to prevent the seal 318 from being blown through the opening 370 under high pressure in the inner cavity 358 of the seal 318.

The resilient member 320 is desirably relaxed or slightly compressed longitudinally in the decompressed state (FIG. 6), and compressed longitudinally in the compressed state (FIG. 7). The resilient member 320 is desirably not attached or bonded to either of the clam shells 322a/322b or the housing 312.

FIG. 7 illustrates compression and FIG. 6 illustrates decompression during valve activation. In the compressed state, the syringe 362 is placed on the seal cap 340 inside the opening 370 of the housing 312, and the application of pressure on the syringe 362 creates pressure on the seal cap 340. The downward pressure pushes the seal cap 340 away from the circular opening 370 and toward the distal lower portion of the housing 312 which has a larger inner diameter, thereby allowing the precut slit 342 to open. The side wall 350 slides over the proximal end 354 of the inner conduit 330, and the resilient member 320 deforms in an accordion-like manner, storing potential energy of the compression. Fluid is able to flow into the syringe 362, or vice versa, depending on whether fluid is to be withdrawn from the patient or medication injected into the patient.

The compression of the seal 318 shown in FIG. 7 generally causes a contraction or reduction in the volume of the inner cavity 358 of the seal 318. The valve 310 has a net gain in volume of the inner cavity 318, however, because the general reduction in volume within the inner cavity 358 is less than an increase in volume within the constricted portion 366 of the inner cavity 358 defined by the clam shells 322a/322b. The expansion results from the movement of the clam shells 322a/322b apart from one another during compression, facilitated by the tapered side wall 324 of the housing 312.

FIG. 6 illustrates the valve after withdrawal of the syringe 362. The seal 318 returns to its decompressed state and essentially fills the opening 370, and the clam shells 322a/322b are pushed proximally toward the opening 370 by the resilient member 320. Because of the contraction of the inner cavity 358 at the constricted portion 366 by the clam shells 322a/322b, there is a net loss or reduction in fluid space, resulting in a positive flow from the valve 310 through, e.g., a catheter tip (not shown). The positive-flow valve 310 advantageously eliminates any dead space during decompression of the seal 318. This is further assisted by the seal 318 with the slit 342 remaining open until the very end, i.e., until the seal cap 340 is squeezed by the upper conduit 384.

In addition, the valve 310 can be reused because the seal 318 can return reversibly in the decompressed state. The seal surface 340 is also swabbable for sterility. Other features of the valve 310 are discussed previously in connection with the first embodiment of this invention and will not be repeated.

Third Embodiment

Figure 8:
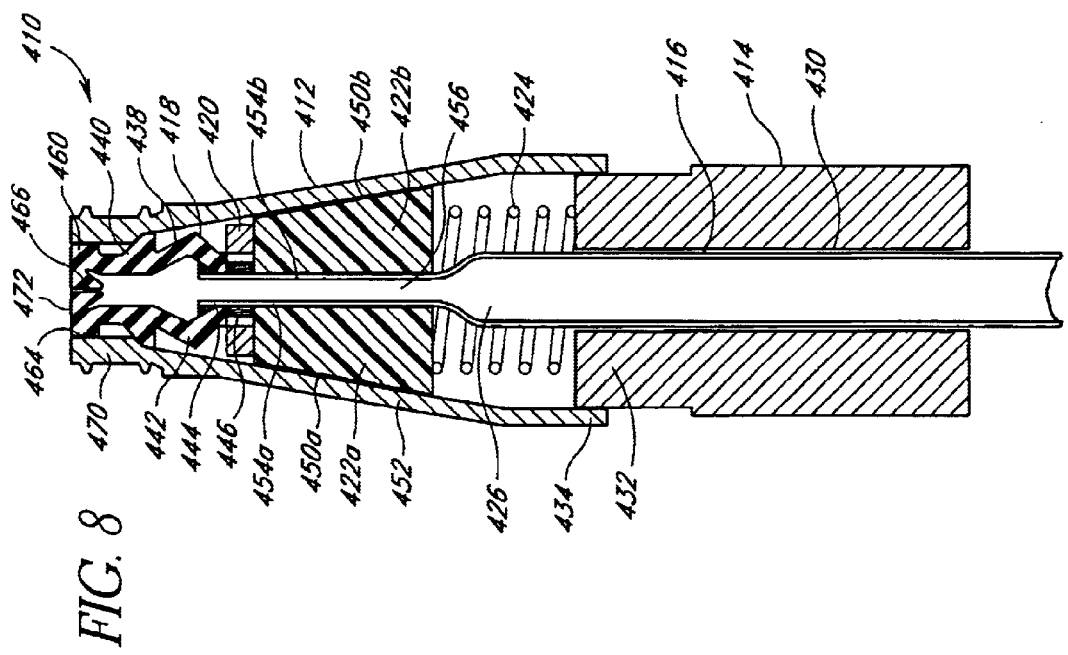
FIG. 8 is a longitudinal cross-sectional view of the third embodiment of the positive-flow valve of this invention before compressing the seal.
Figure 9:
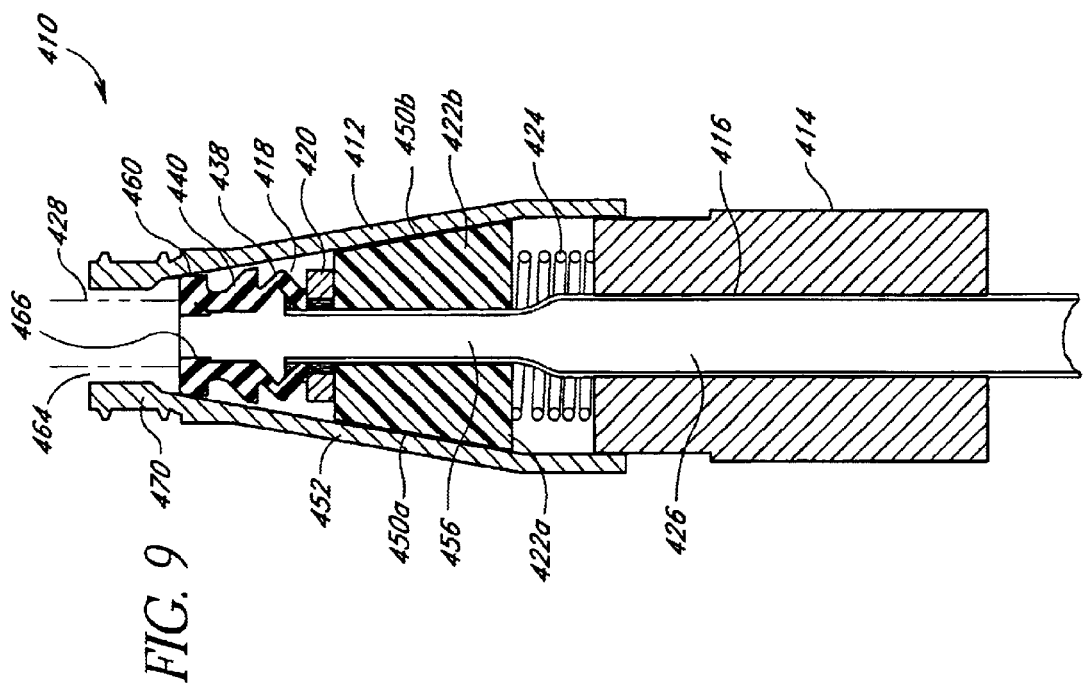
FIG. 9 is a longitudinal cross-sectional view similar to FIG. 8 showing the valve during compression of the seal.

As shown in FIGS. 8 and 9, a third embodiment of the valve 410 of the present invention comprises a valve body or housing 412, a support member 414, a flexible tubing 416, a seal 418, a ring member 420, a pair of clam shells 422a/422b, and a spring 424. The flexible tubing 416 may be connected to a catheter (not shown) and, together with the seal 418, defines an inner cavity 426. The inner cavity 426 forms an expandable fluid space of the valve 410. The clam shells 422a/422b desirably are substantially the same as the clam shells 220a/220b of FIG. 4 and are constructed to cause the fluid space within the valve 410 to increase upon insertion of a medical implement and to decrease upon withdrawal of the medical implement such as a syringe 428 partially shown in phantom in FIG. 9. The housing 412 is desirably similar to the housing 212 of FIG. 4.

The support member 414 has a hollow center 430 which supports the flexible tubing, and a proximal end 432 which encloses a distal end 434 of the housing 412. The support member 414 desirably locks onto the housing 412 via any method known to those of skill in the art. The proximal end 432 of the support member 414 supports the spring 424, which in turn supports the clam shells 422a/422b and seal 418.

The seal 418 is prepared from a resilient material that is flexible, inert, and impermeable to fluid, such as silicon. Referring to FIG. 8, the seal 418 is substantially similar to the seal 210 of FIG. 4, with a portion of the side wall 438 cut off near the shoulder 440 region. As a result, the side wall 438 of the seal 418 is substantially shorter than the side wall 254 of the seal 210 in FIG. 4. A distal end 442 of the side wall 254 is attached, preferably by adhesive, to a proximal end 444 of the flexible tubing 416. The distal end 442 abuts the ring member 420 which is disposed between the seal 418 and the clam shells 422a/422b and attached at its inner surface 446 to a portion of the tubing 416, desirably also by adhesive. Other suitable means of attachment may be used. The ring member 420 is desirably made of polycarbon.

The clam shells 422a/422b desirably form a sliding contact at their proximal ends with the ring member 420 for ease of assembly, but may alternatively be affixed to the ring member 420 by adhesive or similar means. The clam shells 422a/422b are desirably the same as the clam shells 220a/220b of FIG. 4, having tapered external surfaces 450a/450b to cooperate with the tapered side wall portion 452 of the housing 412 for sliding and grooved internal surfaces 454a/454b that cooperate with one another to squeeze a portion of the tubing 416 to form a constricted portion 456.

The spring 424 is substantially the same as the spring 222 of FIG. 4 and serves the same function, being disposed between the distal ends of the clam shells 422a/422b and the proximal end 432 of the support member 414. In the decompressed state shown in FIG. 8, the spring 424 may be relaxed or in slight compression to exert a force on the seal 418 through the clam shells 422a/422b to keep the slit 466 in the seal cap 460 closed. During insertion of the syringe 428, the spring 424 is compressed and stores potential energy from the compression, as illustrated in FIG. 9. Upon withdrawal of the syringe 428, the spring 424 releases the potential energy and pushes the clam shells 422a/422b proximally to close the seal 418, as shown in FIG. 8. The spring 424 is preferably not attached or bonded to either the clam shells 422a/422b or the support member 414 for ease of assembly. The spring 424 can be a helical spring or any other suitable spring known to those with skill in the art.

FIG. 9 shows the compressed state of the valve 410 upon insertion of the syringe 428. In the compressed state, the syringe 428 is placed on the seal cap 460 inside the opening 464 of the housing 412 and the application of pressure on the syringe 428 creates pressure on the seal cap 460. The downward pressure pushes the seal cap 460 away from the circular opening 464 and toward the distal end of the housing 412, which has a larger inner diameter, thereby allowing the precut slit 466 of the seal cap 460 to open. The resilient tubing 416 and the clam shells 422a/422b also move distally as the spring 424 deforms in compression, storing potential energy. Fluid is able to flow into the syringe 428, or vice versa, depending on whether fluid is to be withdrawn from the patient or medication injected into the patient.

The compression of the seal 418 shown in FIG. 9 generally causes a reduction in the volume of the inner cavity 426 formed by the seal 418 and tubing 416. However, because of an expansion of the constricted portion 456 defined by the clam shells 422a/422b an increase in fluid volume is created which is greater than the general reduction in fluid volume within the inner cavity 426, the valve 410 has a net gain in fluid volume. The increase in fluid volume results from the movement of the clam shells 422a/422b apart from one another during seal compression, facilitated by the tapered side wall 452 of the housing 412 and resiliency of the tubing 416.

FIG. 8 illustrates the valve 410 after withdrawal of the syringe 428. The seal 418 returns to its decompressed state and essentially fills the opening 464, and the clam shells 422a/422b are pushed proximally toward the opening 464 by the spring 424. Because of the contraction of the inner cavity 426 at the constricted portion 456 by the clam shells 422a/422b, there is a net loss in fluid space, resulting in a positive flow from the valve 410 through, e.g., a catheter tip (not shown). The positive-flow valve 410 advantageously eliminates any dead space during decompression of the seal 418. This is further assisted by the seal 418, with the slit 466 remaining open until the very end, i.e., until the seal cap 460 is squeezed by upper conduit 470.

In addition, the valve 410 can be reused because the seal 418 can return reversibly to the decompressed state. The seal surface 472 is also swabbable for sterility. Other features of the valve 410 are discussed previously in connection with the earlier embodiments of this invention and will not be repeated.

Fourth Embodiment

Figure 11:
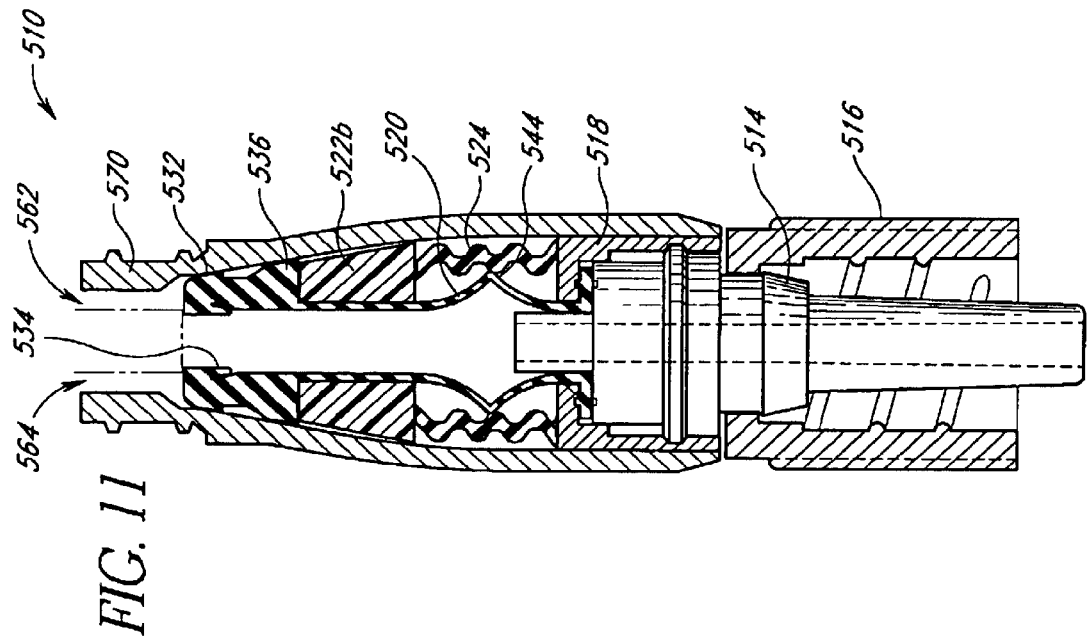
FIG. 11 is a longitudinal cross-sectional view similar to FIG. 10 showing the valve during compression of the seal.
Figure 10:
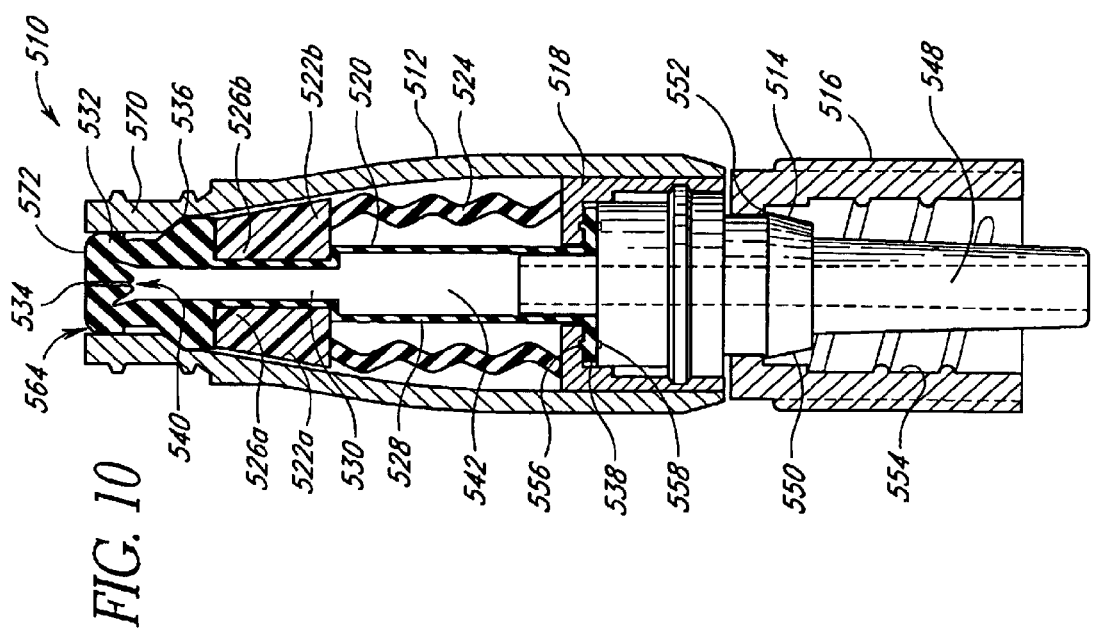
FIG. 10 is a longitudinal cross-sectional view of the fourth embodiment of the positive-flow valve of this invention before compressing the seal.

A fourth embodiment of the present invention is illustrated in FIGS. 10 and 11. As illustrated therein, a valve 510, comprises a valve body or housing 512, a support member 514, a skirt 516, a retaining member 518, a seal 520, a pair of clam shells 522a/522b, and a resilient member 524. The valve 510 has several features that are the same or similar to those of the valve 310 of FIGS. 8 and 9, having a similar resilient member 524 and clam shells 522a/522b. The clam shells 522a/522b have internal surfaces 526a/526b that cooperate with one another to squeeze a portion of the seal side wall 528 to form a constricted portion 530 thereof.

The seal 510 is preferably made of silicon and has a seal cap 532 with a precut slit 534, shoulder 536, lower lip 538, and pressure responsive member 540 that are similar to the seal 210 of FIG. 4. These components serve the same function as those of the seal 210. The side wall 528 may be formed with ringed wall portions 258, as in the seal 210, but FIG. 4 shows the side wall 528 that is generally circular cylindrical. The seal 520 defines an inner cavity 542 which forms an expandable fluid space inside the valve 510. During compression of the seal 520, the side wall 528 deforms outwardly into a circumferential cusp or bulge 544 in the unconstricted region between the clam shells 522a/522b and the support member 514. The side wall 528 returns to its decompressed shape upon decompression of the seal 520. The seal 520 is desirably relaxed longitudinally in the decompressed state (FIG. 10), and compressed longitudinally in the compressed state (FIG. 11). Alternatively, the seal 520 may be stretched longitudinally in tension by the resilient member 524 in the decompressed state and be relaxed or slightly compressed longitudinal in the compressed state.

Referring to FIG. 10, the skirt 516 is a bell-shaped skirt that is similar to the skirt 316 of FIG. 8. The skirt 516 creates a shield for an inner conduit 548 of the support member 514. The inner conduit 548 may be connected to a terminal end of a catheter (not shown) which has an open end that is generally inserted into a patient. The support member 514 serves as a support and attachment device for the seal 520 by holding the seal 520 in place inside the housing 512.

The support member 514 also serves as a support and attachment device for the skirt 516. Similar to the valve 310 of FIG. 8, the support member 514 shown in FIG. 10 has an edge portion 550 which engages a ledge 552 of the skirt 516 in assembly. This attachment secures the skirt 516 in place. The skirt 516 desirably includes a Luer-Lock portion 554 that enables the valve 510 to be removably attached to, for example, a fluid line or catheter connected to a patient.

The retaining member 518 is desirably provided to secure the lower lip 538 of the seal 520 and support the resilient member 524. The retaining member 518 is held inside the housing 512 by the support member 514, and is provided for ease of assembling the valve 510. The retaining member 518 has an annular groove 556, and the support member 514 has an annular groove 558. The annular grooves 556,558 form a locking mechanism to support and secure the seal 520 within the housing 512 by engaging the lower lip 538 snugly with the grooves 556,558. It is noted that a different embodiment may provide a unitary member which replaces the support member 514 and the retaining member 518. It is therefore contemplated that such an embodiment would fall within the scope of this invention.

FIG. 11 illustrates compression and FIG. 10 illustrates decompression during valve activation. In the compressed state, a medical implement such as the syringe 562 partially shown in phantom is placed on the seal cap 532 inside the opening 564 of the housing 512, and the application of pressure on the syringe 562 creates pressure on the seal cap 532. The downward pressure pushes the seal cap 532 away from the circular opening 564 and toward the lower portion of the housing 512, which has a larger inner diameter, thereby allowing the precut slit 534 to open. The side wall 528 deforms outwardly at the unconstricted region into a circumferential cusp 544, and the resilient member 524 deforms in an accordion-like manner, storing potential energy of the compression. Fluid is able to flow into the syringe 562, or vice versa, depending on whether fluid is to be withdrawn from the patient or medication injected into the patient.

The compression of the seal 520 shown in FIG. 11 generally causes a reduction in the fluid volume of the inner cavity 542 of the seal 520. The valve 510 has a net gain in volume of the inner cavity 542, however, because the general reduction in volume within the inner cavity 542 is less than the increase in volume within the constricted portion 530 as defined by the clam shells 522a/522b and of the cusp 544 at the unconstricted region of the seal 520.

FIG. 10 illustrates the valve 510 after withdrawal of the syringe 562. The seal 520 returns to its decompressed state and essentially fills the opening 564, and the clam shells 522a/522b are pushed back up toward the opening 564 by the resilient member 524. Because of the contraction of the inner cavity 542 of the seal 520, there is a net loss in fluid space, resulting in a positive flow from the valve 510 through, e.g., a catheter tip (not shown). The positive-flow valve 510 advantageously eliminates any dead space during decompression of the seal 520. This is further assisted by the seal 520, with the slit 534 remaining open until the very end, i.e., until the seal cap 532 is squeezed by the circular opening 564 at the top of the upper conduit 570.

In addition, the valve 510 can be reused because the seal 520 can return reversibly in the decompressed state. The seal surface 572 is also swabbable for sterility. Other features of the valve 510 are discussed previously in connection with the earlier embodiments of this invention.

Fifth Embodiment

Figure 13:
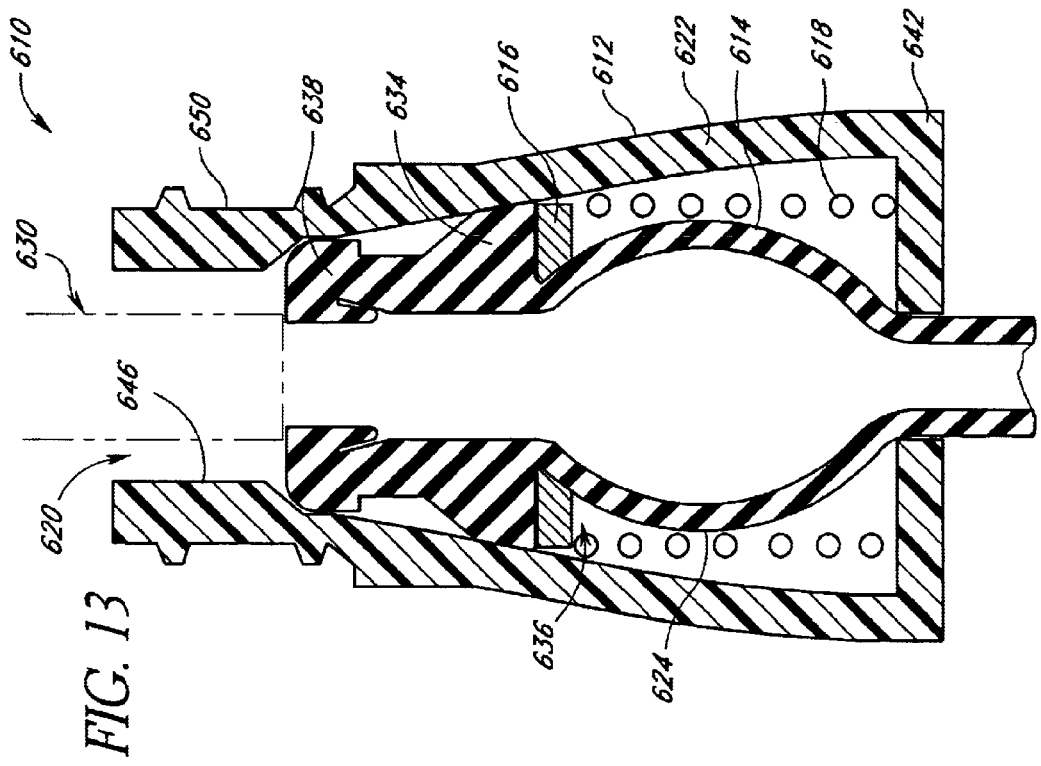
FIG. 13 is a longitudinal cross-sectional view similar to FIG. 12 showing the valve during compression of the seal.
Figure 12:
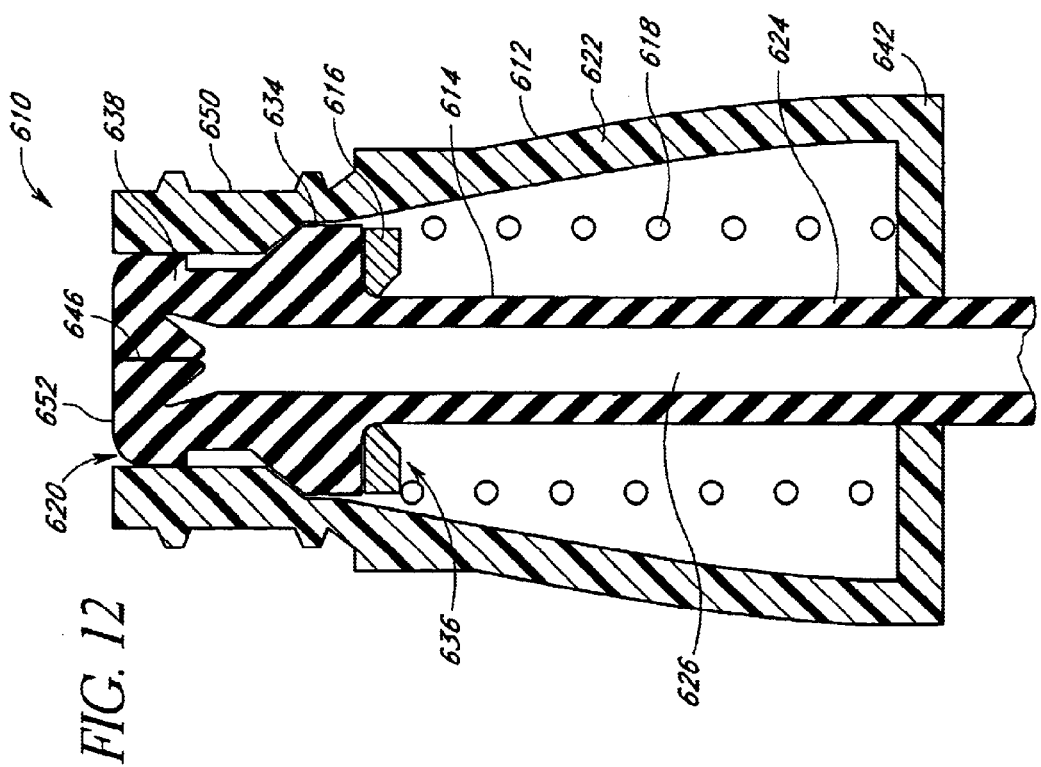
FIG. 12 is a longitudinal cross-sectional view of the fifth embodiment of the positive-flow valve of this invention before compressing the seal.

FIGS. 12 and 13 show a fifth embodiment valve 610 in accordance with the present invention, the valve 610 comprising a valve body or housing 612, a seal 614, a ring member 616, and a spring 618. The housing 612 is similar to the housing 212 of FIG. 4, with a circular opening 620, and a tapered side wall 622, but may have a straight side wall instead. The seal 614 is similar to the seal 318 of FIG. 8, having a substantially cylindrical side wall 624 and defining an inner cavity 626 which forms an expandable fluid space inside the valve 610. The side wall 624 may have different and variable thickness (not shown). The components are dimensioned and configured to cause the fluid space to expand upon insertion of a medical implement and to contract upon withdrawal of the medical implement such as a syringe 630 partially shown in phantom in FIG. 13. The distal portion of the seal 614 is connected to a fluid line such as a catheter (not shown), and may be secured to the housing by means known to those with skill in the art, such as by the use of a support member (not shown) similar to the support member 214 shown in FIG. 15.

The ring member 616 is desirably an annular disk 616 made of a hard plastic and disposed between a shoulder 634 of the seal 614 and a proximal end 636 of the spring 618. The ring member 616 serves as a constraint for the seal 614 during compression and efficiently transfers the compressive force to the spring 618, assisting in the deformation of the seal 614. During decompression, the ring member 616 efficiently transfers the spring force to the seal cap 638 of the seal 614 to close the opening 620. Although the ring member 616 facilitates the deformation and reformation of the seal 614, it is not necessary for the seal 614 to work. In that case, the spring 618 will contact the seal cap 638 directly.

The spring 618 is substantially the same as the spring 222 of FIG. 4 and serves the same function, being disposed between the ring member 616 and a distal end 642 of the housing 612. In an alternative embodiment, the distal end 642 may be a separate component from the housing 612 for ease of assembly. In the decompressed state shown in FIG. 12, the spring 618 may be relaxed or be in slight compression to exert a force on the seal 614 through the ring member 616 to keep the seal 614 closed. During insertion of the syringe 630, the spring 618 is compressed and stores potential energy from the compression, as illustrated in FIG. 13. Upon withdrawal of the syringe 630, the spring 618 releases the potential energy and pushes the ring member 616 to close the seal 616 as shown in FIG. 12. The spring 618 is preferably not fixed with either the ring member 616 or the distal end 642 of the housing 612 for ease of assembly. The spring 618 can be a helical spring or any other suitable spring known to those with skill in the art.

The side wall 624 of the seal 614 is constrained by the ring member 616 and housing 612, and is substantially relaxed in the decompressed state. During compression of the seal 614, the side wall 624 bulges in the unconstrained region between the ring member 616 and the distal end 642 of the housing 612, causing an increase in the fluid space within the valve 610. The side wall 624 returns to its decompressed shape upon decompression of the seal 614. Alternatively, the side wall 624 may be stretched in tension by the spring 618 in the decompressed state and goes through a relaxed position before deforming under compression to its bulged condition.

FIG. 13 illustrates compression and FIG. 12 illustrates decompression during valve activation. In the compressed state, the syringe 630 is placed on the seal cap 638 inside the opening 620 of the housing and the application of pressure on the syringe 630 creates pressure on the seal cap 638. The downward pressure pushes the seal cap 638 and the ring member 616 away from the circular opening 620 and toward the lower portion of the housing 612 which has a larger inner diameter, thereby allowing the precut slit 646 of the seal cap 638 to open. The side wall 624 deforms outwardly and bulges at the unconstricted region, as the spring 618 is compressed, storing potential energy of the compression. Fluid is able to flow into the syringe 630, or vice versa, depending on whether fluid is to be withdrawn from the patient or medication injected into the patient. The compression of the seal 614 shown in FIG. 13 results in a net gain in volume of the inner cavity.

FIG. 12 illustrates the valve 610 after withdrawal of the syringe 630. The seal 614 returns to its decompressed state and essentially fills the opening 620, and the ring member 616 is pushed back up toward the opening 620 as the spring 618 releases its potential energy. Because of the contraction of the inner cavity 626 of the seal 614, there is a net loss in fluid space, resulting in a positive flow from the valve 610 through, e.g., a catheter tip (not shown). The positive-flow valve 610 advantageously eliminates any dead space during decompression of the seal 614. This is further assisted by the seal 614 with the slit 646 remaining open until the very end, i.e., until the seal cap 638 is squeezed by the circular opening 620 at the top of the upper conduit 650 of the housing 612.

In addition, the valve 610 can be reused because the seal 614 can return reversibly in the decompressed state. The seal surface 652 is also swabbable for sterility. Other features of the valve 610 are discussed previously in connection with the earlier embodiments of this invention.

Sixth Embodiment

Figure 15:
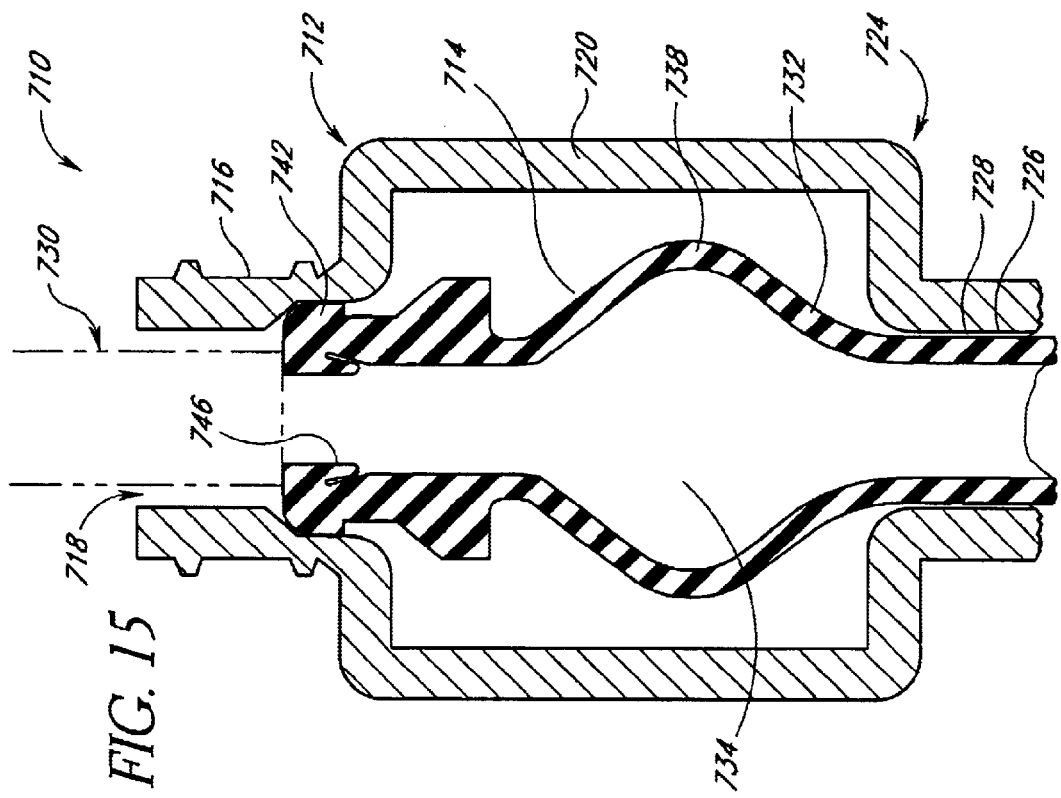
FIG. 15 is a longitudinal cross-sectional view similar to FIG. 14 showing the valve during compression of the seal.
Figure 14:
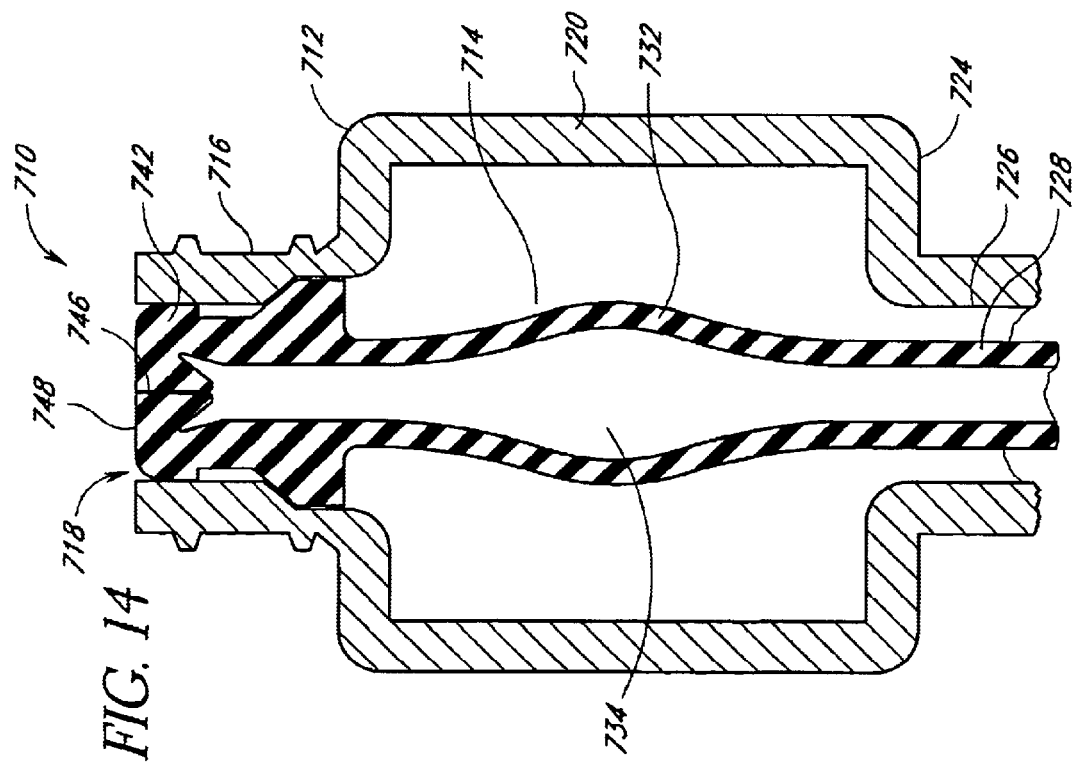
FIG. 14 is a longitudinal cross-sectional view of the sixth embodiment of the positive-flow valve of this invention before compressing the seal.

A sixth embodiment of a valve 710 is illustrated in FIGS. 14 and 15. The valve 710 comprises a valve body or housing 712 and a seal 714. The housing 712 has an upper conduit 716 near a proximal end with a circular opening 718 that is preferably adapted to receive a medical implement. A side wall portion 720 is protruded to facilitate deformation of the seal 714. A distal end 724 of the housing 712 forms a lower passage 726 (partially shown) which supports and constrains a distal portion 728 of the seal 714, and is connected, for example, to a fluid line such as a catheter (not shown). Alternatively, a support member (not shown) may be used to detachably lock onto the housing 712 and support the seal 714, such as those shown in FIG. 4 (214) or FIG. 12 (514).

The seal 714 is generally similar to the seal 614 of FIGS. 12 and 13, and has a substantially cylindrical side wall 721, although the side wall 732 may have a slight bulge 733 as shown in FIG. 14. It defines an inner cavity 734 which forms an expandable fluid space inside the valve 710. In the decompressed state, the seal 714 is constrained by the upper conduit 716 and lower passage 726 of the housing 712, and is substantially relaxed in the decompressed state. The components are dimensioned and configured to cause the fluid space to expand or increase upon insertion of the medical implement and to contract or decrease upon withdrawal of the medical implement such as the syringe 730 partially shown in phantom in FIG. 15. During compression of the seal 714, the side wall 732 bulge in the unconstrained region between the upper conduit 716 and lower passage 726 and the bulge 738 is substantially round. The side wall 732 return to its decompressed shape upon decompression of the seal 714.

FIG. 15 illustrates compression and FIG. 14 illustrates decompression during valve activation. In the compressed state, the syringe 730 is placed on the seal cap 742 of the seal 714 inside the opening 718 of the housing 712 and the application of pressure on the syringe 730 creates pressure on the seal cap 742. The downward pressure pushes the seal cap 742 away from the circular opening 718 and toward the protruded portion 720 of the housing 712 which has a larger inner diameter, thereby allowing the precut slit 746 of the seal cap 742 to open. The side wall 732 deforms outwardly and bulges at the unconstricted region 738, storing potential energy of the compression. Fluid is able to flow into the syringe 730, or vice versa, depending on whether fluid is to be withdrawn from the patient or medication injected into the patient. The compression of the seal 714 shown in FIG. 15 generates a net gain in volume of the inner cavity.

FIG. 14 illustrates the valve 710 after withdrawal of the syringe 730. The seal 714 returns to its decompressed state and essentially fills the opening 718. Because of the contraction of the inner cavity 734 of the seal, there is a net loss in fluid space, resulting in a positive flow from the valve 710 through, e.g., a catheter tip (not shown). The positive-flow valve 710 advantageously eliminates any dead space during decompression of the seal 714. This is further assisted by the seal 714 with the slit 746 remaining open until the very end, i.e., until the seal cap 742 is squeezed by the circular opening 718 at the top of the upper conduit 716.

In addition, the valve 710 can be reused because the seal 710 can return reversibly in the decompressed state. The seal surface 748 is also swabbable for sterility. Other features of the valve 710 are discussed previously in connection with the earlier embodiments of this invention.

Seventh Embodiment

Figure 17:
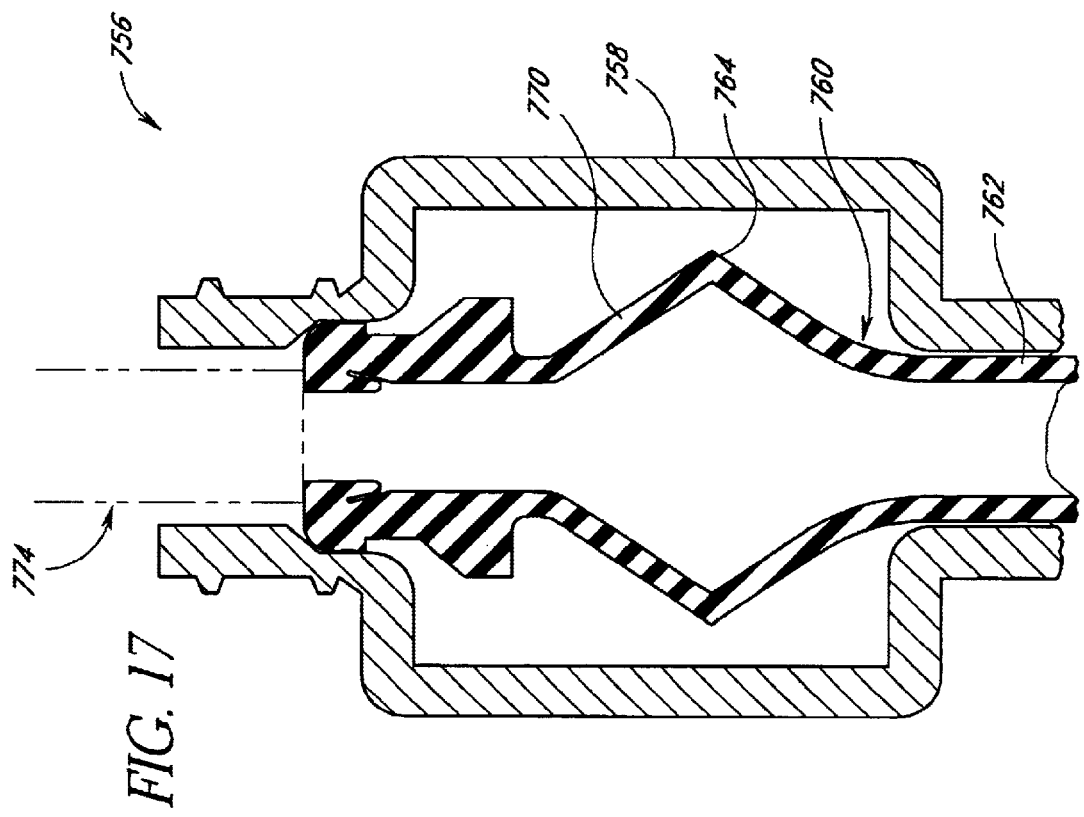
FIG. 17 is a longitudinal cross-sectional view similar to FIG. 16 showing the valve during compression of the seal.
Figure 16:
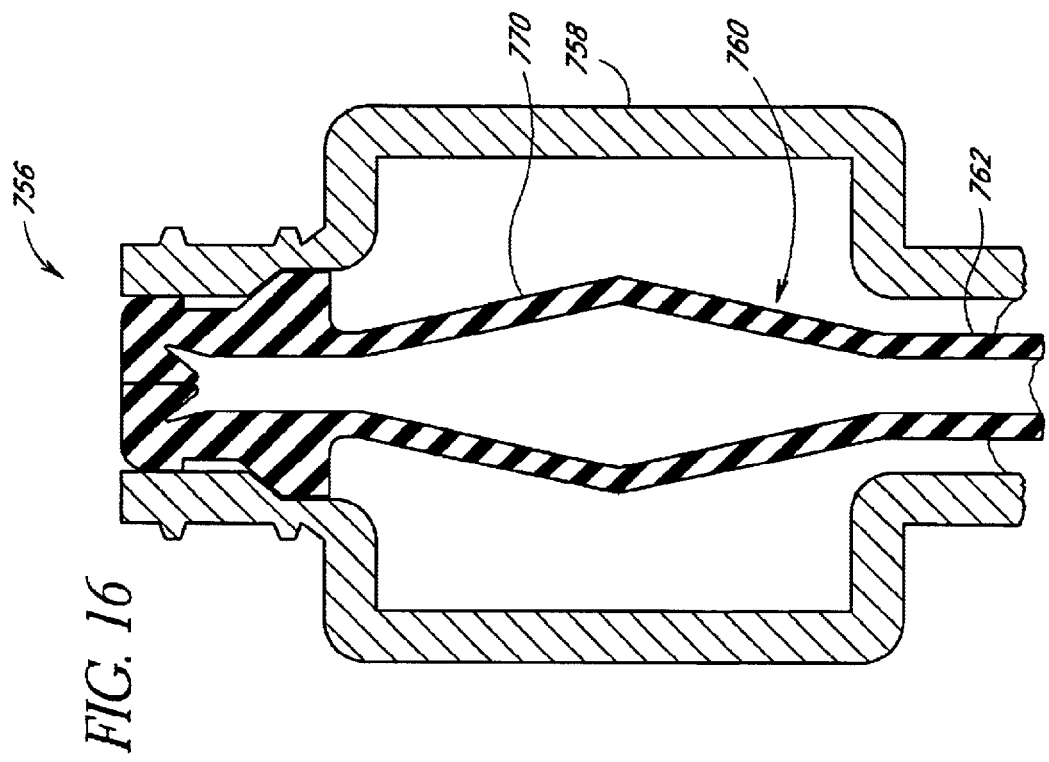
FIG. 16 is a longitudinal cross-sectional view of the seventh embodiment of the positive-flow valve of this invention before compressing the seal.

FIGS. 16 and 17 illustrate a valve 710 in accordance with a seventh embodiment of the present invention, the valve 756 comprising a valve body or housing 758 and a seal 760 that are substantially the same as the housing 712 and seal 714 of FIGS. 14 and 15, with a distal portion 762 of the seal 760 connected to a fluid line such as a catheter (not shown). The seal 760, however, is configured to deform upon compression into a diamond-shaped cusp 764 instead of a round bulge 738 as illustrated in FIGS. 14 and 15. This type of construction may facilitate deformation and reformation of the seal 760, and may be more easily formed. The valve activation of this embodiment is virtually identical to that in FIGS. 14 and 15, except for the deformed shape of the seal side wall 770. It is contemplated, therefore, that a seal that may deform into a variety of shapes other than round and diamond shapes to achieve positive flow may be employed, as long as the it is dimensioned and configured to cause the fluid space of the valve to expand upon insertion of a medical implement and to contract upon withdrawal of the medical implement such as the syringe 774 partially shown in phantom in FIG. 28.

Eighth Embodiment

As illustrated in FIGS. 18 and 19, an eighth embodiment valve 810 of the present invention is similar to the embodiments shown in FIGS. 14–17. The valve 810 also includes a housing 812 having an internal cavity 814 with an upper conduit 816, and a seal 818 disposed inside the internal cavity 814 and having an inner cavity 820 that defines a fluid space. The housing 812 has a distal end 824 which supports a side wall 826 of the seal 818. A distal portion 828 of the seal 818 is connected to a fluid line such as a catheter (not shown). The pressure at the inner cavity 820 of the seal 818 is P1. Between the housing 812 and the seal 818 is an enclosed pressure chamber 832 at pressure P2. The valve activation utilizes the pressure difference between P2 in the pressure chamber 832 and P1 in the inner cavity 820 of the seal 818.

Upon insertion of a medical implement such as a syringe 836 shown in phantom in FIG. 19, the pressure at the inner cavity 820 of the seal 818 increases from P1 to P3 and the fluid space inside the seal 818 expands from the decompressed state of FIG. 18. The expansion of the fluid space results primarily from a difference in pressure between P3 and P2. This valve 810 is particularly advantageous in the case where the side wall 826 of the seal 818 deforms without storing substantial potential energy. For instance, the side wall 826 of the seal 818 may deform without substantial resistance or resiliency such as a membrane, or the seal is not constrained longitudinal by the distal portion 824 of the housing 812 and may slide in and out of the internal cavity 814 of the housing 812 through the distal end 824.

FIG. 19 illustrates compression and FIG. 18 illustrates decompression during valve activation. In the compressed state, the syringe 836 is placed on the seal cap 838 of the seal 818 inside the opening 840 of the housing 812 and the application of pressure on the syringe creates pressure on the seal cap 838. The downward pressure pushes the seal cap 838 away from the circular opening 840 and toward the lower portion of the housing 812 which has a larger inner diameter, thereby allowing the precut slit 844 of the seal cap 838 to open. The entry of the fluid causes the pressure at the inner cavity 814 of the seal 812 to increase to P3. As a result, the side wall 826 deforms outwardly and bulges at the unconstricted region 848. Potential energy is stored in the change in pressure differential between the inner cavity 820 and the pressure chamber 832. The side wall 826 of the seal 818 need not deform and store energy, but may do so. Fluid is able to flow into the syringe 836, or vice versa, depending on whether fluid is to be withdrawn from the patient or medication injected into the patient. The compression of the seal 818 shown in FIG. 19 causes a net gain or increase in fluid volume within the inner cavity.

FIG. 18 illustrates the valve 810 after withdrawal of the syringe 836. The seal 818 returns to its decompressed state and essentially fills the opening 840, and the pressure in the inner cavity 820 returns to P1 and releases the potential energy. Because of the contraction of the inner cavity 820 of the seal 818, there is a net loss in fluid space, resulting in a positive flow from the valve 810 through, e.g., a catheter tip (not shown). The positive-flow valve 810 advantageously eliminates any dead space during decompression of the seal 818. This is further assisted by the seal 818 with the slit 844 remaining open until the very end, i.e., until the seal cap 838 is squeezed by the circular opening 840 at the top of the upper conduit 816.

In addition, the valve 810 can be reused because the seal 818 can return reversibly in the decompressed state. The seal surface 854 is also swabbable for sterility. Other features of the valve 810 are discussed previously in connection with the earlier embodiments of this invention.

Ninth Embodiment

Figure 21:
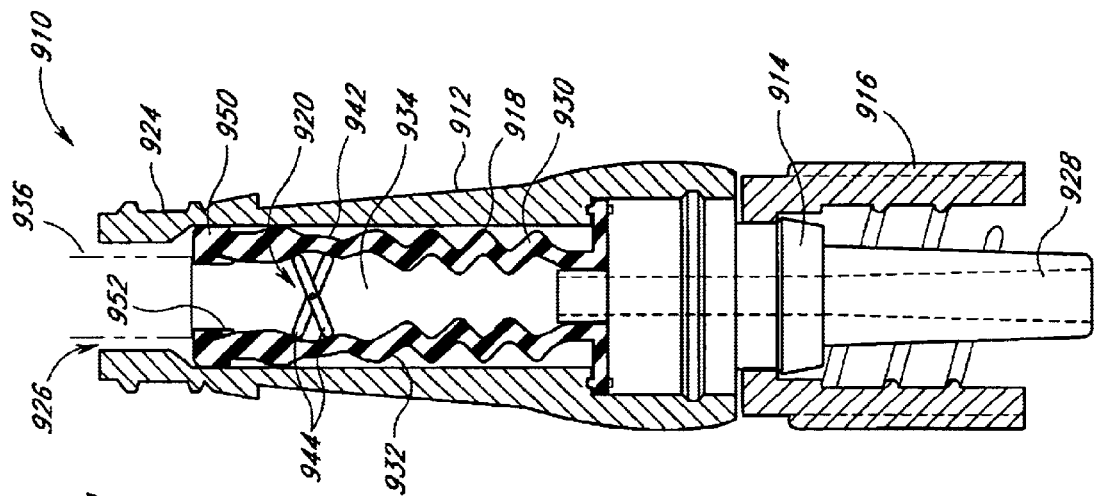
FIG. 21 is a longitudinal cross-sectional view similar to FIG. 20 showing the valve during compression of the seal.
Figure 20:
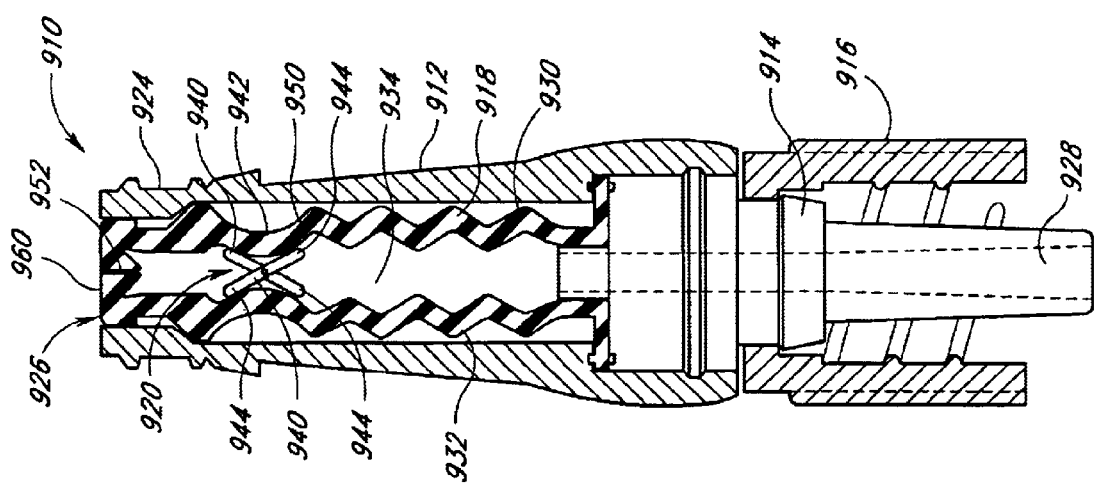
FIG. 20 is a longitudinal cross-sectional view of the ninth embodiment of the positive-flow valve of this invention before compressing the seal.

A ninth embodiment of a valve 910 comprising a housing 912, a support member 914, a skirt 916, a seal 918, and a scissor-like cross member 920, is depicted in FIGS. 20 and 21. The housing 912 has an upper conduit 924 with a circular opening 926. The support member 914 has an inner conduit 928 which is connected to a fluid line such as a catheter (not shown). The seal 918 has a side wall 930 desirably formed of alternating wall portions 932 and defines an inner cavity 934 which forms an expandable fluid space inside the valve 910. The cross member 920 is dimensioned and configured to assist in causing the fluid space to expand upon insertion of a medical implement and to contract upon withdrawal of the medical implement such as the syringe 936 partially shown in phantom in FIG. 21.

The cross member 920 has two longitudinal member 940 attached together which rotates with respect to one another, and is desirably made of a hard material such as a hard plastic. The cross member 920 is disposed at a constricted portion 942 of the seal 918 within the inner cavity 934 with the longitudinal members 940 preferably substantially disposed vertically. The ends 944 of the longitudinal members 940 are desirably attached to the side wall 930 as shown in FIG. 20. The longitudinal members 940 rotate to a substantially horizontal orientation upon compression by the insertion of the syringe 936 as shown in FIG. 21. This rotation is referred to as the deformation of the cross member 920. The longitudinal members 940 may be attached to rotate freely with respect to one another. Alternatively, the longitudinal members 940 may be spring-loaded or attached such that they rotate under a rotational force but reform to their relaxed position upon release of the force. Upon withdrawal of the syringe 936 as shown in FIG. 20, the longitudinal members 940 return to the substantially vertical positions, referred to as the reformation of the cross member 920. The longitudinal members 940 are desirably longitudinal plates 940 with sufficient width to expand the constricted portion 942 of the seal 918 in the substantially horizontal position but not so wide that they impedes flow therethrough. Alternatively, they may contain holes (not shown) through which fluid can pass.

FIG. 21 illustrates compression and FIG. 20 illustrates decompression during valve activation. In the compressed state, the syringe 926 is placed on the seal cap 950 of the seal 918 inside the opening 926 of the housing 912 and the application of pressure on the syringe 936 creates pressure on the seal cap 950. The downward pressure pushes the seal cap 950 away from the circular opening 926 and toward the lower portion of the housing 912 which has a larger inner diameter, thereby allowing the precut slit 952 of seal cap 950 to open. The side wall 930 of the seal 918 deforms in an accordion-like manner, and the cross member 920 deforms and opens up the constricted portion 922 of the seal 918, storing potential energy of the compression. Fluid is able to flow into the syringe 936, or vice versa, depending on whether fluid is to be withdrawn from the patient or medication injected into the patient. The compression of the seal 918 and deformation of the cross 920 shown in FIG. 21 generally causes a contraction of the volume of the inner cavity 934 of the seal 918. The valve 910 has a net gain in volume of the inner cavity 934, however, because the general contraction of the inner cavity 934 is less than by the expansion of the constricted portion 942 pushed apart by the cross member 920. The expansion results from the movement of the longitudinal members 940 of the cross member 920 during compression.

FIG. 20 illustrates the valve 910 after withdrawal of the syringe 936. The seal 918 returns to its decompressed state and essentially fills the opening 926, and the cross member 920 reforms to allow the constricted region 942 of the seal 918 to narrow. Because of the contraction of the inner cavity 934 at the constricted portion 942, there is a net loss in fluid space, resulting in a positive flow from the valve 910 through, e.g., a catheter tip (not shown). The positive-flow valve 910 advantageously eliminates any dead space during decompression of the seal 918. This is further assisted by the seal 918 with the slit 952 remaining open until the very end, i.e., until the seal cap 950 is squeezed by the circular opening 926 at the top of the upper conduit 924.

In addition, the valve 910 can be reused because the seal 918 can return reversibly in the decompressed state. The seal surface 960 is also swabbable for sterility. Other features of the valve 910 are discussed previously in connection with the earlier embodiments of this invention.

Tenth Embodiment

Figure 23:
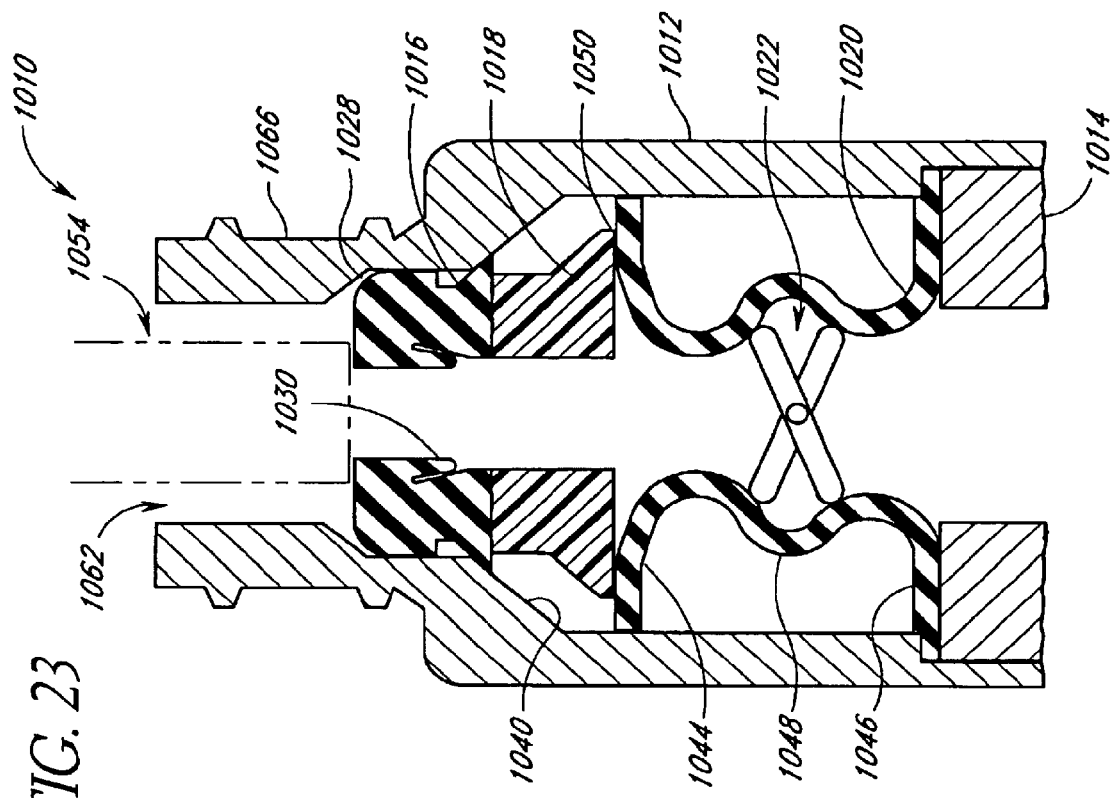
FIG. 23 is a longitudinal cross-sectional view similar to FIG. 22 showing the valve during compression of the seal.
Figure 22:
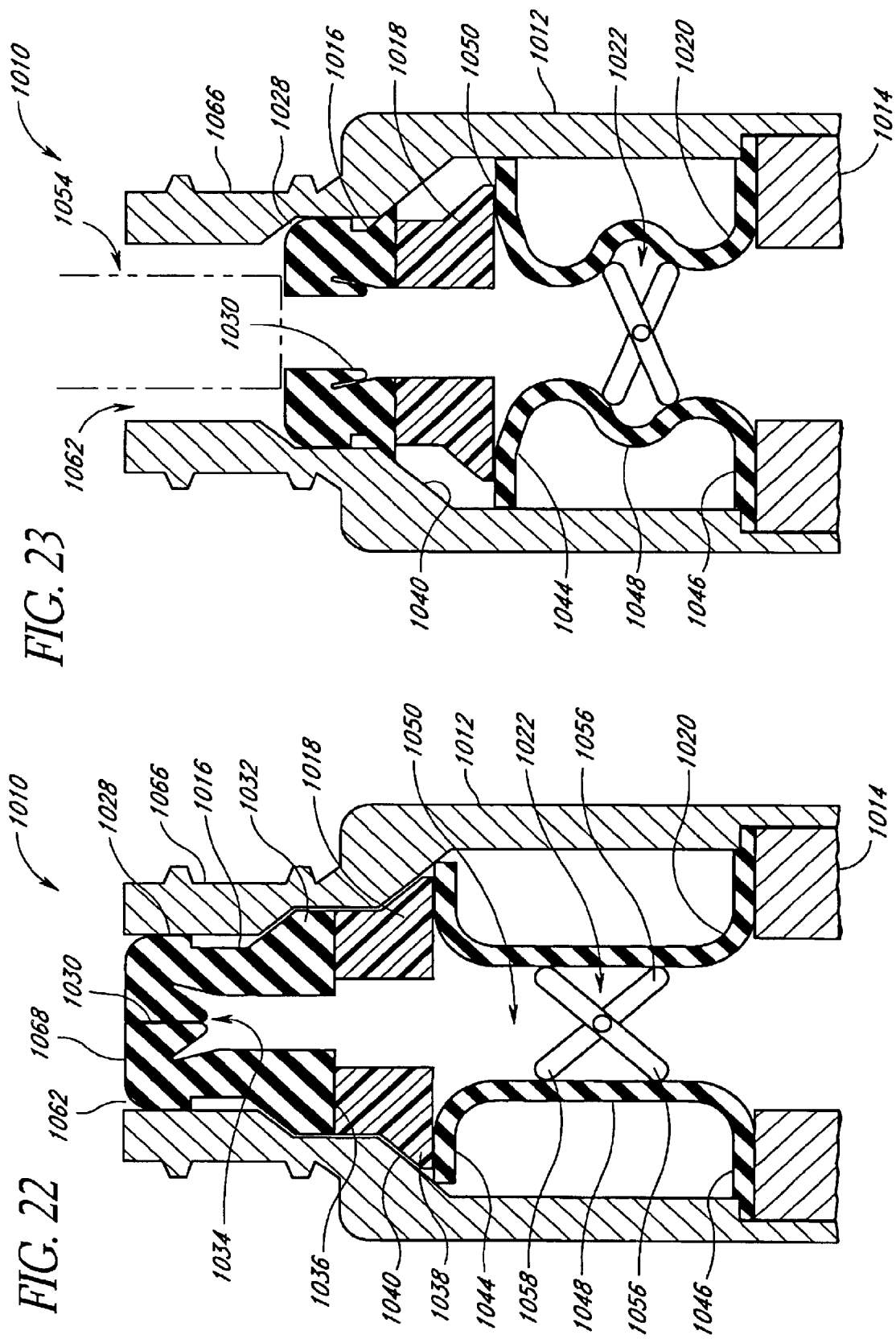
FIG. 22 is a longitudinal cross-sectional view of the tenth embodiment of the positive-flow valve of this invention before compressing the seal.

FIGS. 22 and 23 illustrate a valve 1010 in accordance with a tenth embodiment of the present invention, the valve 1010 comprising a valve body or housing 1012, a support member 1014 (partially shown), a seal 1016, a ring member 1018, a resilient reel 1020, and a scissor-like cross member 1022. The support member 1014 has an inner conduit (not shown) which is connected to a fluid line such as a catheter (not shown). The seal 1016 has a seal cap 1028 with slit 1030, shoulder 1032, and pressure responsive member 1034.

The ring member 1018 forms a sliding contact with a distal end 1036 of the seal 1016 and is preferably made from a hard plastic. The ring member 1018 desirably has a shoulder 1038 which is constrained by a ledge 1040 of the housing 1012 in the upward direction. The distal end of the ring member 1018 contacts an upper flange 1044 of the resilient reel 1020 and facilitates transfer of the compressive force due to insertion of a medical implement to cause deformation of the reel 1020. The reel 1020 is made from a material that is flexible, inert, and impermeable to fluid, such as silicon. It has a lower flange 1046 that is supported and secured by the support member 1014 and a central body portion 1048 that is substantially cylindrical. The seal 1016, ring member 1018, and resilient reel 1020 define an inner cavity 1050 which forms an expandable fluid space inside the valve 1010.

The cross member 1022 is substantially the same of the cross member 920 of FIGS. 20 and 21 and is dimensioned and configured to assist in causing the fluid space to increase upon insertion of a medical implement and to decrease upon withdrawal of the medical implement such as the syringe 1054 partially shown in phantom in FIG. 23. The cross member 1022 has two longitudinal members 1056 rotatably attached together. The cross member 1022 is disposed adjacent the central body portion 1048 of the reel 1020 within the inner cavity 1050 with the longitudinal members 1056 preferably pointed toward the vertical direction and desirably attached to the central body portion 1048 at its four ends 1058 as shown in FIG. 22. The longitudinal members 1056 rotate to a substantially horizontal orientation upon compression by the insertion of the syringe 1054 as shown in FIG. 23. This rotation is referred to as the deformation of the cross member 1022. The longitudinal members 1050 may be attached to rotate freely with respect to one another. Alternatively, the longitudinal members 1056 may be spring-loaded or attached such that they rotate under a rotational force but reform to their relaxed position upon release of the force. Upon withdrawal of the syringe 1056 as shown in FIG. 22, the longitudinal members 1056 return to the substantially vertical positions, referred to as the reformation of the cross member 1022. The longitudinal members 1026 are desirably longitudinal plates 1056 with sufficient width to open up the central body portion 1048 of the reel 1020 in the substantially horizontal position but not so wide that they impedes flow therethrough. Alternatively, they may contain holes (not shown) through which fluid can pass.

FIG. 23 illustrates compression and FIG. 22 illustrates decompression during valve activation. In the compressed state, the syringe 1054 is placed on the seal cap 1028 inside the opening 1062 of the housing 1012 and the application of pressure on the syringe 1054 creates pressure on the seal cap 1028. The downward pressure pushes the seal cap 1028 away from the circular opening 1062 and toward the lower portion of the housing 1012 which has a larger inner diameter, thereby allowing the precut slit 1030 to open. The ring member 1018 moves toward the support member 1014 and compresses the resilient reel 1020. The upper flange 1044 of the resilient reel 1020 is pushed by the ring member 1018 toward the lower flange 1046. The central body portion 1048 bulges outwardly as the cross member 1022 deforms, storing potential energy of the compression. Fluid is able to flow into the syringe 1054, or vice versa, depending on whether fluid is to be withdrawn from the patient or medication injected into the patient.

The compression of the seal 1016 and deformation of the cross 1022 shown in FIG. 23 generally causes a reduction in the volume of the inner cavity of the seal 1016. The valve 1010 has a net gain in volume of the inner cavity 1050, however, because the expansion of the central body portion 1048 of the flexible reel 120 causes an increase in fluid volume which reduction resulting in is greater than the general contraction of the inner cavity 1050. The expansion results from the movement of the longitudinal members 1056 of the cross member 1022 to open up the central body portion 1048 of the resilient reel 1020 during compression.

FIG. 22 illustrates the valve 1010 after withdrawal of the syringe 1054. The seal 1016 returns to its decompressed state and essentially fills the opening 1062, and the cross member 1022 reforms to allow the central body region 1048 of the resilient reel 1022 to narrow. Because of the contraction of the inner cavity 1050 at the central body portion 1048, there is a net loss in fluid space, resulting in a positive flow from the valve 1010 through, e.g., a catheter tip (not shown). The positive-flow valve 1010 advantageously eliminates any dead space during decompression of the seal 1016. This is further assisted by the seal 1016 with the slit 1030 remaining open until the very end, i.e., until the seal cap 1028 is squeezed by the circular opening 1062 at the top of the upper conduit 1066 of the housing.

In addition, the valve 1010 can be reused because the seal 1016 can return reversibly in the decompressed state. The seal surface 1068 is also swabbable for sterility. Other features of the valve 1010 are discussed previously in connection with the earlier embodiments of this invention.

Eleventh Embodiment

An eleventh embodiment of a valve 1110 in accordance with the present invention is illustrated in FIGS. 24 and 25, and comprises a valve body or housing 1112 and a seal 1114. The housing 1112 has an upper conduit 1116 near a proximal end with a circular opening 1118 that is preferably adapted to receive a medical implement such as a syringe 1120 partially shown in phantom in FIG. 25. The housing 1112 has a lower conduit 1124 (partially shown) near a distal end which is connected to a fluid line such as a catheter (not shown). Disposed between the upper conduit 1116 and lower conduit 1124 are protruded right and left side walls 1126a, 1126b connected to resilient ribbed portions 1128a,1128b which allow the side walls 1126a,1126b to be stretched outwardly and reform inwardly in a substantially horizontal direction. Aside from the resilient ribbed portions 1128a, 1128b, the rest of the housing 1112 is desirably made of a firm material such as a hard plastic.

The seal 1114 is generally similar to the seal 318 of FIG. 6 with a similar shoulder 1132, seal cap 1134, and pressure responsive element 1136. The cylindrical side wall 350 of FIG. 6, however, is replaced with a spreader 1140, which includes two legs 1142a,1142b that extend from the shoulder 1132 outwardly at distal ends 1144a,1144b that bear against the protruded right and left side walls 1126a,1126b, as best seen in FIG. 24. The distal end 1144a may be attached to the protruded side wall 1126a, and the distal end 1144b may be attached to the protruded side wall 1126b, by adhesives or other available means. An inner cavity 1150 is formed by the seal 1114 and a distal portion 1152 of the housing 1112, and defines a fluid space of the valve 1110. During compression of the seal 1114, the spreader 1140 extends further outwardly and pushes the protruded side walls 1126a,1126b outwardly. The seal 1114 and housing 1112 are configured and dimensioned to assist in causing the fluid space to expand upon insertion of the medical implement 1120 and to contract upon withdrawal of the medical implement 1120.

FIG. 25 illustrates compression and FIG. 24 illustrates decompression during valve activation. In the compressed state, the syringe 1120 is placed on the seal cap 1134 inside the opening 1118 of the housing 1112 and the application of pressure on the syringe 1120 creates pressure on the seal cap 1134. The downward pressure pushes the seal cap 1134 away from the circular opening 1118 and toward the lower portion of the housing 1112 which has a larger inner diameter, thereby allowing the precut slit 1156 oft he seal cap 1134 to open. The spreader 1140 extends outwardly, stretching the resilient ribbed portions 1128a,1128b and pushing the protruded right and left side walls 1126a,1126b of the housing 1112 outwardly, storing potential energy of the compression. Fluid is able to flow into the syringe 1120, or vice versa, depending on whether fluid is to be withdrawn from the patient or medication injected into the patient. The compression of the seal 1114 and deformation of the spreader 1140 shown in FIG. 36 results in a net gain in volume of the inner cavity 1150.

FIG. 24 illustrates the valve 1110 after withdrawal of the syringe 1120. The seal 1114 returns to its decompressed state and essentially fills the opening 1118, and the spreader 1140 and resilient ribbed portions 1128a,1128b reform to allow the protruded right and left side walls 1126a,1126b to move inwardly. Because of the contraction of the inner cavity 1150, there is a net loss in fluid space, resulting in a positive flow from the valve 1110 through, e.g., a catheter tip (not shown). The positive-flow valve 1110 advantageously eliminates any dead space during decompression of the seal 1114. This is further assisted by the seal 14 with the slit 1156 remaining open until the very end, i.e., until the seal cap 1134 is squeezed by the circular opening 1156 at the top of the upper conduit 1116.

In addition, the valve 1110 can be reused because the seal 1114 can return reversibly in the decompressed state. The seal surface 1160 is also swabbable for sterility. Other features of the valve 1110 are discussed previously in connection with the earlier embodiments of this invention.

Twelfth Embodiment

Figures 26, 27:
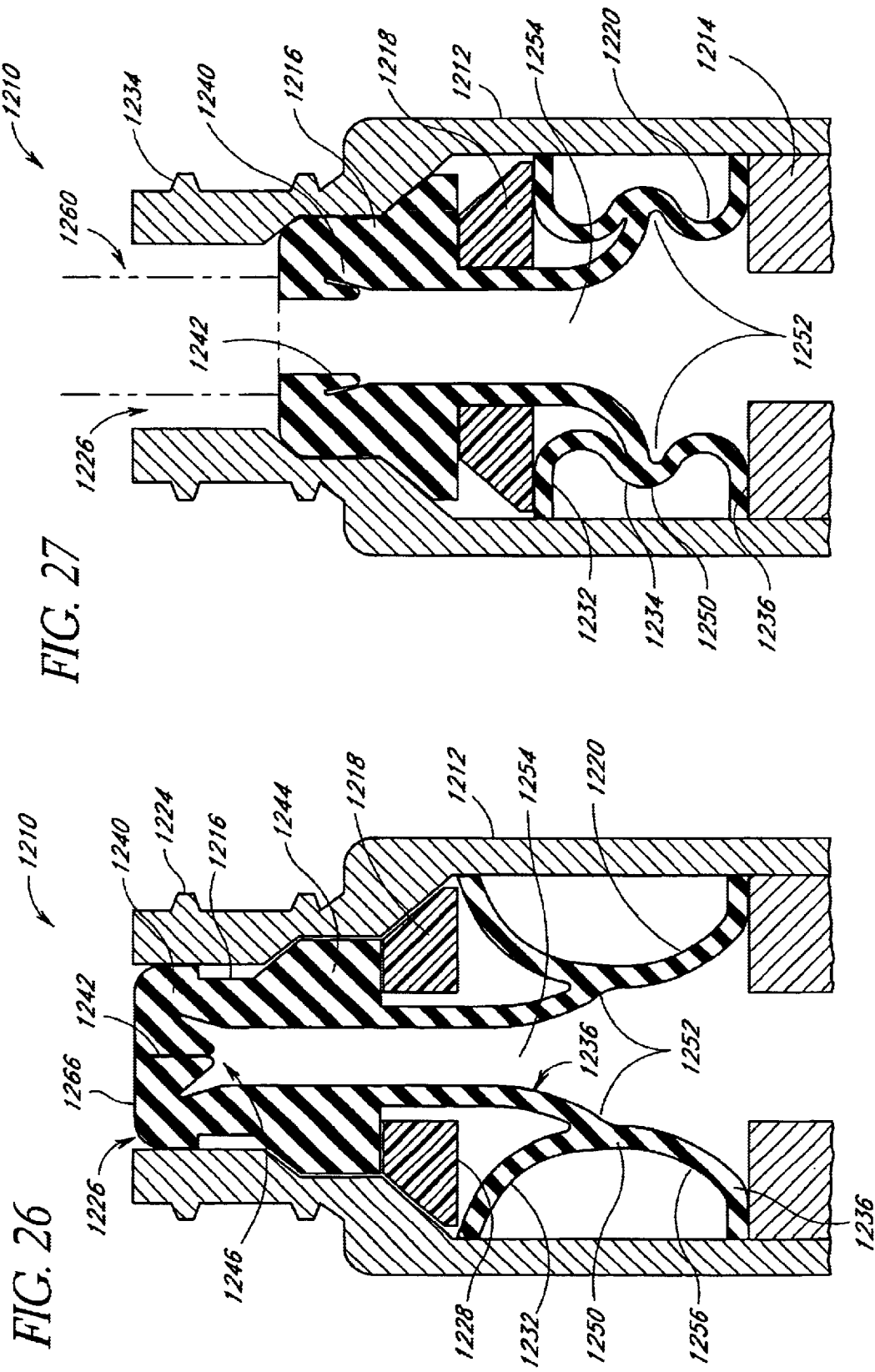
FIG. 26 is a longitudinal cross-sectional view of the twelfth embodiment of the positive-flow valve of this invention before compressing the seal.
FIG. 27 is a longitudinal cross-sectional view similar to FIG. 26 showing the valve during compression of the seal.

A twelfth embodiment valve 1210 is illustrated in FIGS. 26 and 27, and comprises a valve body or housing 1212, a support member 1214 (partially shown), a seal 1216, a ring member 1218, and a resilient reel 1226. The housing 1212, support member 1214, and ring member 1218 are substantially the same as those shown in FIGS. 22 and 23. The housing 1212 has an upper conduit 1224 with a circular opening 1226. The support member 1214 has an inner conduit (not shown) which is connected to a fluid line such as a catheter (not shown). The distal end 1228 of the ring member 1218 contacts an upper flange 1232 of the resilient reel 1220 and facilitates transfer of the compressive force due to insertion of a medical implement such as a syringe to cause deformation of the reel 1220. The reel 1220 further includes a central body portion 1234 and a lower flange 1236 that is desirably supported and secured by the support member 1214.

The seal 1216 is similar to the seal 1114 of FIGS. 24 and 25, and has a similar seal cap 1240 with slit 1242, shoulder 1244, and pressure responsive member 1246. The seal 1246 has a spreader 1250 that extends from the shoulder 1244 outwardly and forms a circular distal ring 1252 that bears against the central body portion 1234 of the resilient reel 1220, as best seen in FIG. 26. The distal ring 1252 may be attached to the central body portion 1234 by adhesives or other available means. An inner cavity 1254 is formed by the seal 1216 and a distal portion 1256 of the resilient reel, and defines a fluid space of the valve 1210. During compression of the seal 1216, the spreader 1250 extends further outwardly and pushes the central body portion 1234 of the resilient reel 1220 outwardly. The seal 1216 and resilient reel 1220 are configured and dimensioned to assist in causing the fluid space to increase upon insertion of a medical implement and to decrease upon withdrawal of the medical implement such as the syringe 1260 partially shown in phantom in FIG. 27.

FIG. 27 illustrates compression and FIG. 26 illustrates decompression during valve activation. In the compressed state, the syringe 1260 is placed on the seal cap 1240 inside the opening 1226 of the housing 1212 and the application of pressure on the syringe 1260 creates pressure on the seal cap 1240. The downward pressure pushes the seal cap 1240 away from the circular opening 1226 and toward the lower portion of the housing 1212 which has a larger inner diameter, thereby allowing the precut slit 1242 to open. The ring member 1218 moves toward the support member 1214 and compresses the resilient reel 1220. The upper flange 1232 of the resilient reel 1220 is pushed by the ring member 1214 toward the lower flange 1236. The central body portion 1234 bulges outwardly as the spreader 1250 deforms and pushes the central body portion 1234 outwardly, storing potential energy of the compression. Fluid is able to flow into the syringe 1260, or vice versa, depending on whether fluid is to be withdrawn from the patient or medication injected into the patient.

The compression of the seal 1216 and deformation of the spreader 1250 and reel 1220 shown in FIG. 27 causes an increase in volume of the inner cavity 1254 because of the expansion of the central body portion 1234 of the flexible reel 1220. The expansion results from the movement of the spreaders 1250 to open up the central body portion 1234 of the resilient reel 1220 during compression.

FIG. 26 illustrates the valve 1210 after withdrawal of the syringe 1260. The seal 1216 returns to its decompressed state and essentially fills the opening 1226, and the spreader 1250 reforms to allow the central body region 1234 of the resilient reel 1220 to narrow. Because of the contraction of the inner cavity 1254 at the central body portion 1234, there is a net loss in fluid space, resulting in a positive flow from the valve 1210 through, e.g., a catheter tip (not shown). The positive-flow valve 1210 advantageously eliminates any dead space during decompression of the seal 1216. This is further assisted by the seal 1216 with the slit 1242 remaining open until the very end, i.e., until the seal cap 1240 is squeezed by the circular opening 1226 at the top of the upper conduit 1224.

In addition, the valve 1210 can be reused because the seal 1216 can return reversibly in the decompressed state. The seal surface 1266 is also swabbable for sterility. Other features of the valve 1210 are discussed previously in connection with the earlier embodiments of this invention.

Thirteenth Embodiment

Figure 28:
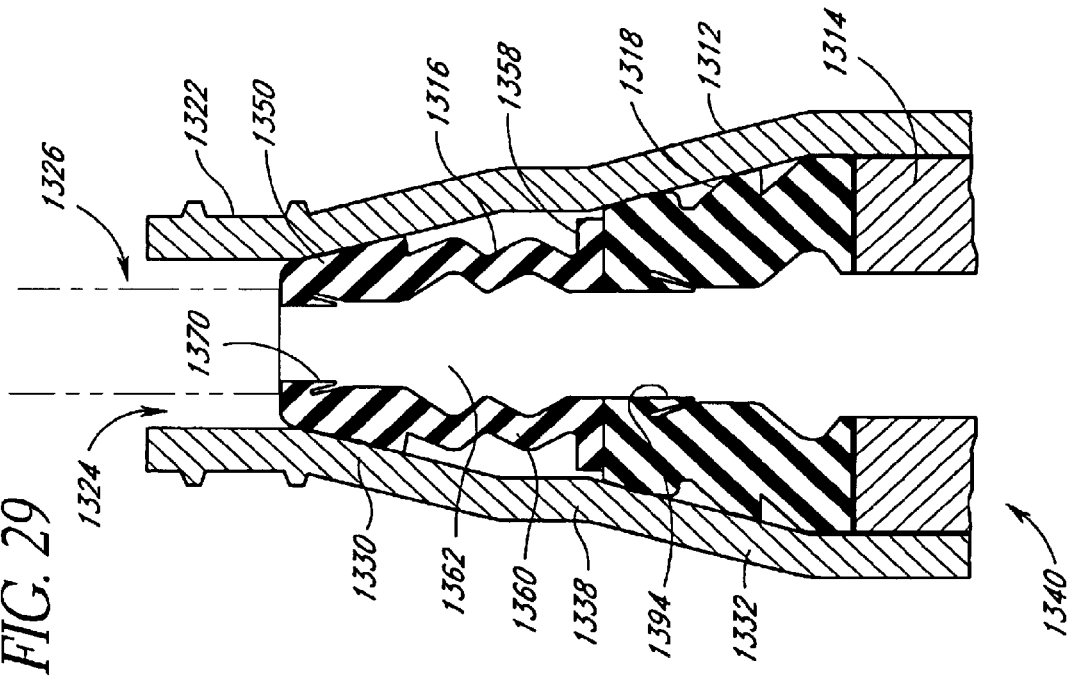
FIG. 28 is a longitudinal cross-sectional view of the thirteenth embodiment of the positive-flow valve of this invention before compressing the seal.
Figure 29:
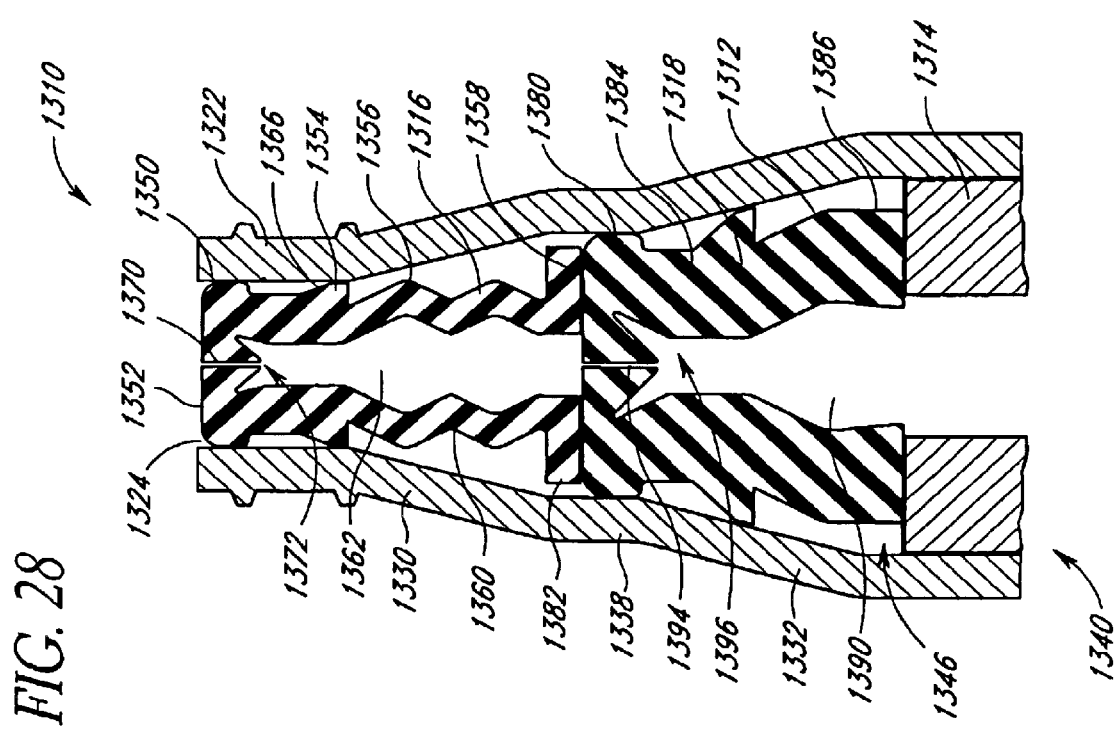
FIG. 29 is a longitudinal cross-sectional view similar to FIG. 28 showing the valve during compression of the seal.

A thirteenth embodiment valve 1310 in accordance with the present invention is illustrated in FIGS. 28 and 29. The valve 1310 comprises a body or housing 1312, a support member 1314 (partially shown), an upper seal 1316, and a lower seal 1318. The housing 1312 has an upper conduit 1322 near a proximal end with a circular opening 1324 that is preferably adapted to receive a medical implement such as a syringe 1326 partially shown in phantom in FIG. 40. The body 1312 has an upper side wall 1330 distal to the upper conduit 1322 that is desirably circular in cross section with a diameter larger than the diameter of the circular opening 1324. The body 1312 has a lower side wall 1332 distal to the upper side wall 1330 with a diameter larger than the diameter of the upper side wall 1330. A middle conduit 1338 is advantageously formed between the upper side wall 1330 and lower side wall 1332. The upper side wall 1330 is advantageously tapered from the upper conduit 1322 to the middle conduit 1338 and the lower side wall 1332 is advantageously tapered from the middle conduit 1338 to a distal end 1340 of the housing 1312. The middle conduit 1338 has a diameter larger than the diameter of the upper conduit 1322 and smaller than the diameter of the distal end 1340 of the housing 1312.

The support member 1314 has at its distal end an inner conduit (not shown) which may be connected to a terminal of a catheter (not shown). The support member 1314 serves as a support and attachment device for the upper and lower seals 1316, 1318 by holding the seals 1316, 1318 in place inside the internal cavity 1346 of the housing 1312.

The upper and lower seals 1316, 1318 are prepared from a resilient material that is flexible, inert, and impermeable to fluid, such as silicon. The upper seal 1316 has a seal cap 1350 with a generally flat top surface 1352, a shoulder 1354, a side wall 1356, and a base 1358. The side wall 1356 advantageously is comprised of ringed wall portions 1360 which deform in an accordion-like fashion and assist in the reformation of the seal 1316 to enclose the housing opening 1324 upon withdrawal of the syringe 1326. During compression of the upper seal 1316, the diameter of the ringed wall portions 1360 expand outwardly in the radial direction. The interior of the upper seal 1316 is hollow to provide an upper inner cavity 1362, as best seen in FIG. 28. The shoulder 1354 engages an upper ledge 1366 provided in the upper conduit 1322 of the housing 1312 such that the upper ledge 1366 confines the movement of the shoulder 1354 toward the opening 1324 to prevent the upper seal 1316 from being blown through the opening 1324 under high pressure in the upper inner cavity 1362 of the seal 1316.

The seal cap 1350 of the upper seal 1316 reseals in the valve 1310 at the opening 1324 with the top surface 1352 of the seal 1316 flush with or above the opening 1324 upon removal of the medical implement 1326. The seal cap 1350 substantially fills the opening 1324 in the top of the upper conduit 1322. It is preferred the top surface 1352 be exposed after assembly so that it may be swabbed with alcohol or other disinfectant. The seal cap 1350 of the upper seal 1316 desirably has a unique shape with a precut slit 1370 such that the seal cap 1350 is squeezed shut by the opening 1324 when assembled and the slit 1370 opens automatically during compression. The seal 1316 desirably also includes a pressure responsive member 1372 to further assist in creating a fluid-tight seal in the decompressed state.

As shown in FIGS. 28 and 29, the lower seal 1318 desirably is generally similar to the upper seal 1316. The lower seal has a similar seal cap 1380 with a generally flat top surface 1382, a shoulder 1384, and a side wall 1386. The side wall 1386 defines a lower inner cavity 1390 and may include similar ringed wall portions (not shown). The seal cap 1380 is disposed at the middle conduit 1338 at the decompressed state and reseals the lower inner cavity 1390 at the middle conduit 1338 upon removal of the medical implement 1326. The lower inner cavity 1390 forms a fluid space of the valve 1310, being in fluid communication through the lower conduit (not shown) to, e.g., a catheter (not shown). The valve components are configured and dimensioned to assist in causing the fluid space to increase upon insertion of the medical implement 1326 and to decrease upon withdrawal of the medical implement 1326.

The seal cap 1380 advantageously provides a fluid tight seal, having a shape and a precut slit 1394 similar to those of the upper seal 1316. The lower seal 1318 also includes desirably a pressure responsive member 1396 similar to the pressure responsive member 1372 of the upper seal 1316. The components of the lower seal 1318 are generally larger than those of the upper seal 1316 because of the geometry of the valve housing 1312.

To illustrate valve activation, FIG. 29 shows the compressed state of the valve 1310 upon insertion of the syringe 1326. The syringe 1326 is placed on the upper seal cap 1350 inside the opening 1324 of the housing 1212. The application of pressure on the syringe 1326 creates pressure on the seal cap 1330, and the resulting downward pressure compresses the upper seal 1316. This pushes the seal cap 1350 away from the circular opening 1324 and toward the middle conduit 1338 at a region with a larger inner diameter, thereby allowing the precut slit 1370 to open. The downward movement is facilitated by the compression of the ringed wall portions 1360 of the side wall 1356 of the upper seal 1316. The downward force is transferred to the lower seal 1318 through the base 1358 of the upper seal 1316 which cooperates with the seal cap 1380 of the lower seal 1318. The application of the pressure pushes the lower seal cap 1380 away from the middle conduit 1338 and toward the lower portion of the housing 1312 which has a larger inner diameter, thereby allowing the precut slit 1394 to open. Fluid is now able to flow into the syringe 1326, or vice versa, depending on whether fluid is to be withdrawn from the patient or medication injected into the patient. FIG. 29 shows the valve 1310 opened by insertion of the syringe 1326 into the opening 1324.

In the compressed state shown in FIG. 29, the fluid space generally contract under pressure from the decompressed state shown in FIG. 28. Upon removal of the syringe 1326 from the upper conduit 1322, as shown in FIG. 28, the upper and lower seals 1316,1318 are free to move toward their decompressed states. The movement normally would cause a general expansion of the fluid space. However, because of the fluid communication between the upper inner cavity 1362 and lower inner cavity 1390, and the closing of the precut slit 1394 of the lower seal 1318 upon compression, a decrease in volume results in the lower inner cavity 1390 of the valve 1310. The decrease in the fluid space advantageously generates a positive flow from the valve 1310 through, e.g., a catheter tip (not shown) to eliminate dead space. Advantageously, any dead space within the upper inner cavity 1362 is also minimized since, as the syringe 1326 is withdrawn, the slit 1370 remains open until the very end, i.e., until the seal cap 1350 is squeezed by the circular opening 1324 at the top of the upper conduit 1322. The elimination of backflash is particularly advantageous in the case where the valve 1310 is connected through a catheter to a patient, because it prevents the introduction of blood into the catheter.

As the upper seals 1316 is free to move to its decompressed state, it essentially fills the circular opening 1324. The ability of the upper seal 1316 to return reversibly to its decompressed state, together with the resiliency of the lower seal 1318, permits the reuse of the valve 1310. Following disconnection, and before reuse, the surface 1352 of the seal cap 1316 is essentially flush with the opening 1324 of the housing 1312. Thus, this flush surface 1352 can advantageously be sterilized with alcohol or other surface decontaminating substances. A cover cap (not shown) can further be used to fit over the upper conduit to protect the surface 1352 of the seal cap 1350.

Fourteenth Embodiment

Figure 30:
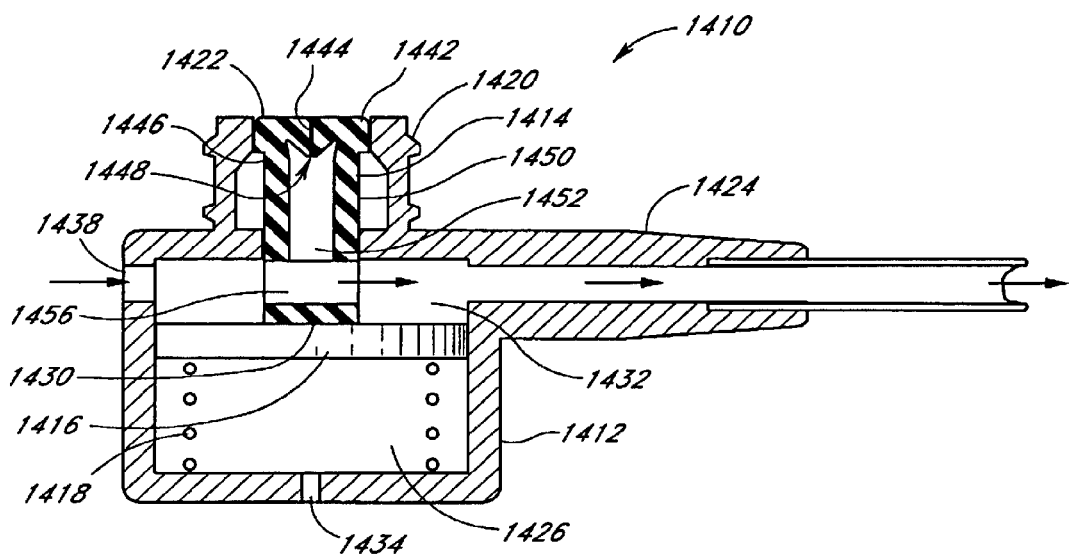
FIG. 30 is a longitudinal cross-sectional view of the fourteenth embodiment of the positive-flow valve of this invention before compressing the seal.
Figure 32:
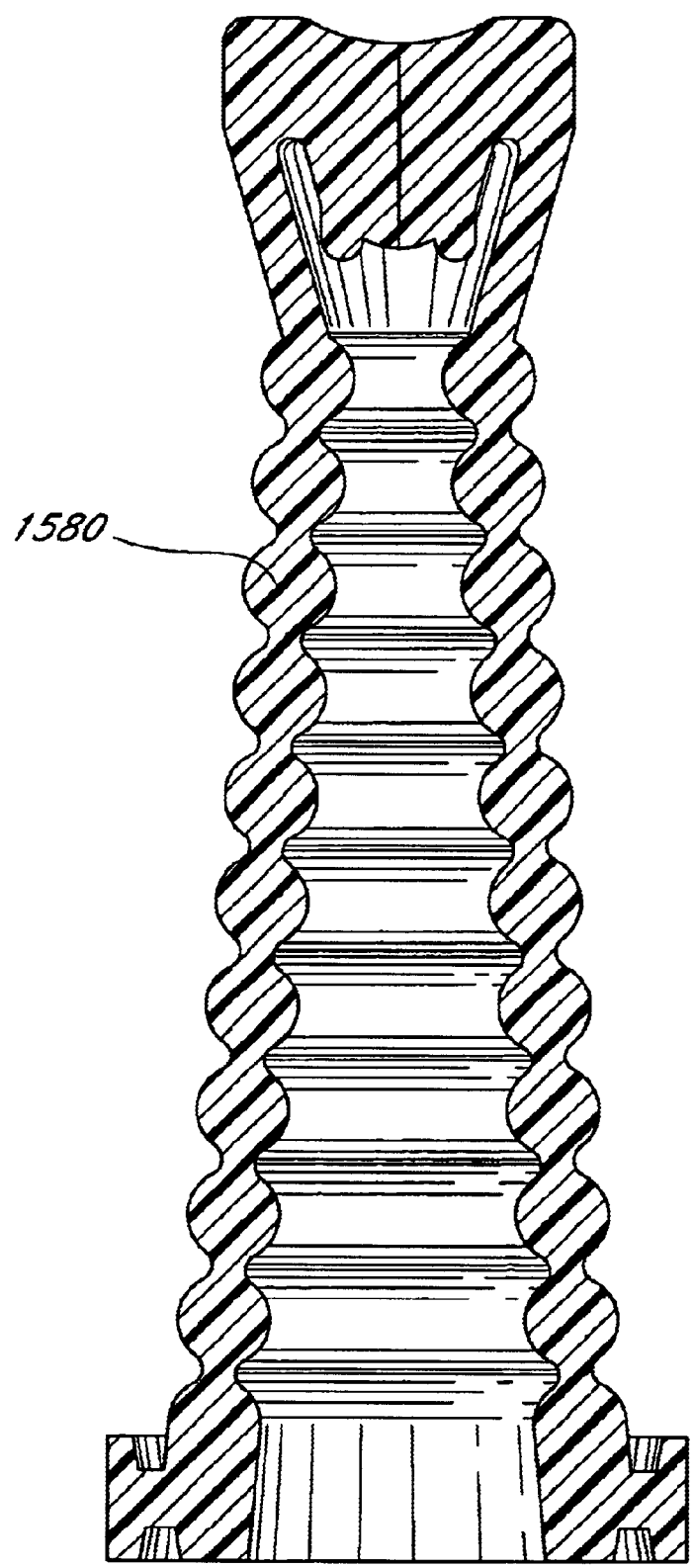
FIG. 32 is a longitudinal cross-sectional view of an alternative seal with a side wall formed with circular tires.

A fourteenth embodiment of a valve 1410 of the present invention is illustrated in FIGS. 30 and 32, and comprises a valve body or housing 1412, a seal 1414, a piston 1416, and a spring 1418. The housing 1412 has an upper conduit 1420 near a proximal end with a circular opening 1422 that is preferably adapted to receive a medical implement such as a syringe 1423 partially shown in phantom in FIG. 30. The housing 1412 has a side conduit 1424 which is connected to a fluid line such as a catheter (not shown). Disposed in a lower chamber 1426 of the housing 1412 is the spring 1418 supporting the piston 1416 which bears against a distal end 1430 of the seal 1414 disposed in an upper chamber 1432 of the housing 1412. The lower chamber 1426 of the housing 1412 advantageously includes an orifice 1434 for venting the air therein to facilitate movement of the spring 1418. The upper chamber 1432 and lower chamber 1426 expand and contract according to the movement of the piston 1416 under pressure from the seal 1414 and the spring 1418. The housing 1412 advantageously includes a side aperture 1438 additional fluid to be transferred to the patient through the upper chamber 1432 and side conduit 1424 when necessary.

The seal 1414 has seal cap 1442 with precut slit 1444, a shoulder 1446, and a pressure responsive member 1448. The seal has a side wall 1450 which defines an inner cavity 1452 and has the distal end 1430 that cooperates with the piston 1416 for efficient transfer of pressure between them. Near the distal end 1430 of the seal 1414 is desirably a transverse fluid passage 1456 for fluid communication between the seal 1414 and the upper chamber 1432. Although FIGS. 30 and 32 illustrate that the transverse fluid passage 1456 also facilitates fluid flow between the side aperture 1438 and the side conduit 1424, it need not do so if fluid can flow around the seal 1414 in the upper chamber 1432. The upper chamber 1432 and the inner cavity 1450 of the seal 1414 forms the fluid space of the valve 1410.

Figure 31:
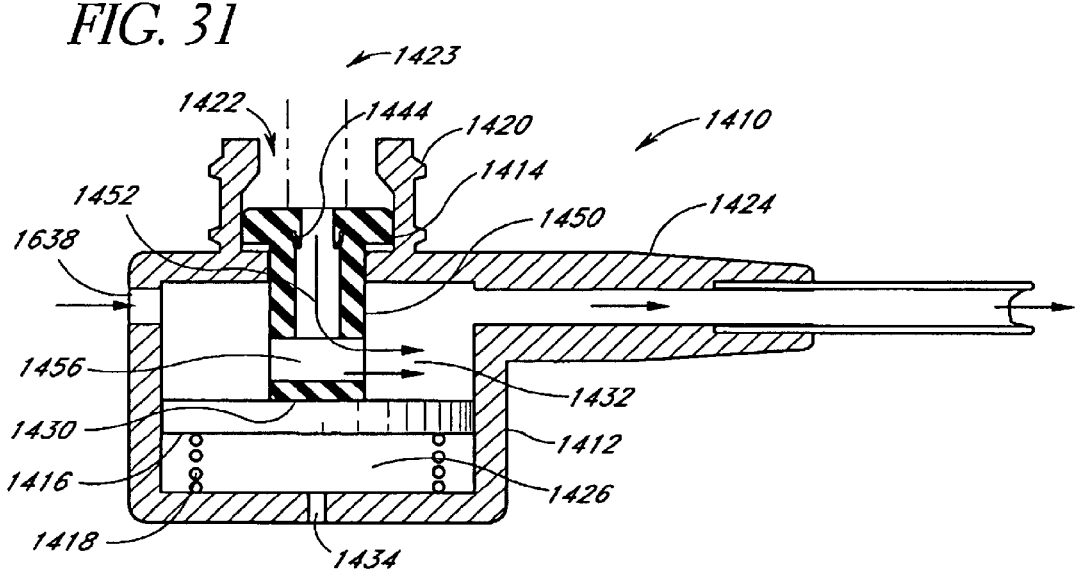
FIG. 31 is a longitudinal cross-sectional view similar to FIG. 30 showing the valve during compression of the seal.

FIG. 31 illustrates compression and FIG. 30 illustrated decompression during valve activation. In the compressed state, the syringe 1423 is placed on the seal cap 1442 inside the opening 1422 of the housing 1412 and the application of pressure on the syringe 1423 creates pressure on the seal cap 1442. The downward pressure pushes the seal cap 1442 away from the circular opening 1422 and toward the lower portion of the housing 1412 which has a larger inner diameter, thereby allowing the precut slit 1444 to open. The side wall 1450 moves further into the upper chamber 1432 and pushes the piston 1476 downward against the spring 1418, which is compressed, storing potential energy of the compression. Fluid is able to flow into the syringe 1423, or vice versa, depending on whether fluid is to be withdrawn from the patient or medication injected into the patient. The compression of the seal 1414 shown in FIG. 42 generates a net gain or increase in volume of the fluid space of the valve 1410.

FIG. 30 illustrates the valve 1410 after withdrawal of the syringe 1423. The seal 1414 returns to its decompressed state and essentially fills the opening 1422, and the piston 1416 moves back to its decompressed position as the spring 1418 releases its potential energy. Because of the contraction of the upper chamber 1432 of the housing 1412, there is a net loss in fluid space, resulting in a positive flow from the valve 1410 through, e.g., a catheter tip (not shown). The positive-flow valve 1410 advantageously eliminates any dead space during decompression of the seal 1414. This is further assisted by the seal 141 with the slit 1444 remaining open until the very end, i.e., until the seal cap 1442 is squeezed by the circular opening 1422 at the top of the upper conduit 1420.

In addition, the valve 1410 can be reused because the seal 1414 can return reversibly in the decompressed state. The seal surface 1460 is also swabbable for sterility. Other features of the valve 1410 are discussed previously in connection with the earlier embodiments of this invention.

Additional Embodiments

Additional embodiments of the present invention are contemplated without departing from the spirit and scope of the present invention. For instance, the volume inside a straight tubing contracts when the tube is bent. Thus, one valve embodiment valve may have a fluid space inside a straight tubing which bends upon insertion of a medical implement and reforms upon withdrawal of the medical implement, thereby effecting positive flow.

In addition, many of the ringed side wall of the seals (such as the portions 1360 of the seal 1316 of FIG. 28) can be replaced by circular tires 1580 stacked in series one on top of an adjacent larger-diameter lower tire, as illustrated in FIG. 32. The circular tires 1580 are preferably solid throughout the diameter of the cross-section thereof Like the ringed side wall portions 1360, these circular tires 1580 will deform and reform upon, respectively, compression and decompression of the seal.

CONCLUSION

In the embodiments described above, the fluid space inside the valve increases upon insertion of a medical implement in the compressed state and decreases upon withdrawal of the medical implement in the decompressed state. In some embodiments, the structure defining the fluid space is substantially relaxed and does not store substantial amount of potential energy. Insertion of the medical implement causes a change in the structure that allows it to store potential energy. The potential energy is released upon withdrawal of the medical implement and the structure returns to a substantially relaxed condition. In other embodiments, at least some components of the structure defining the fluid space stores potential energy under strain or deformation. Upon insertion of a medical implement in the compressed state, the potential energy in those components is released and is stored in other components of the structure or in another form. The stored potential energy in the compressed state is released when the medical implement is removed, and the original potential energy is restored in the structure.

The above presents a description of the best mode contemplated of carrying out the present invention, and of the manner and process of using it, in such full, clear, concise, and exact terms as to enable any person skilled in the art to which it pertains to make and use this invention. This invention is, however, susceptible to modifications and alternate constructions from that discussed above which are fully equivalent. In particular, many of the features of the co-pending applications, serial nos. and can be incorporated into the present invention, and these applications are incorporated herein by reference. The embodiments described are meant to be illustrative and not exhaustive. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention.

What is claimed is:

1. A medical valve adapted to facilitate fluid flow between a male luer and an intravenous fluid line connected to a patent, comprising:
    a body having a cavity in fluid communication with an intravenous fluid line and an opening adapted to receive a male luer, said body having an axial centerline extending through said body, said cavity comprising a neck portion located adjacent said opening and a larger diameter main portion adjacent said neck portion; and
    a sealing device in the cavity and movable between a closed position in which said sealing device prevents fluid flow through said cavity and an open position in which fluid flow is permitted through said cavity, said sealing device comprising:
        a non-deformable reaction member extending across a substantial part of said cavity main portion for automatically increasing and decreasing fluid space in the cavity, said reaction member adapted to reciprocate along said centerline;
        a sealing cap located along said centerline at said opening for engagement by said male luer;
        a cylindrical shaft located along said centerline between said sealing cap and said reaction member, the shaft being movable axially into and out of said neck portion, said shaft: having a smaller diameter than said reaction member, said shaft substantially filling the neck portion when said sealing device is in said closed position and the fluid space in said main portion increasing when said sealing device is in said open position so that said fluid space automatically and reversibly increases in size when said male luer is connected to said connector and which contracts in size when said male luer is disconnected;
        a chamber positioned in said body isolated from said fluid space, said chamber adapted to expand and contract when said sealing device moves between said closed position and said open position; and
        a spring positioned in said chamber and engaging said reaction member for biasing said sealing device into said closed position.

2. The medical valve of claim 1, wherein said sealing cap further comprises a slit.

3. The medical valve of claim 1, wherein said sealing cap further comprises a pressure responsive member on the inside surface thereof to facilitate sealing of said slit.

4. The medical valve of claim 1, wherein a potion adjacent to said opening of said body comprises one or more screw theads.

5. The medical valve of claim 1, wherein the surface of the sealing cap is adapted to be swabable.

6. The medical valve of claim 1, wherein said sealing device further comprises a shoulder.

7. The medical valve of claim 6, wherein a portion adjacent to said opening of said body comprises one or more screw threads.

8. A medical valve adapted to facilitate fluid flow between a male luer and an intravenous fluid line connected to a patient, comprising:

a body having a cavity in fluid communication with an intravenous fluid line and an opening adapted to receive a male luer, said body having an axial centerline extending through said body, said cavity comprising a neck portion located adjacent said opening and a larger diameter main portion adjacent said neck portion; and a sealing device disposed in the cavity and movable between a closed position in which said sealing device prevents fluid flow through said cavity and an open position in which fluid flow is permitted through said cavity, said sealing device comprising:

a rigid disk shaped piston mounted within said cavity and extending across a substantial part of said cavity main portion, said piston adapted to reciprocate along said centerline;

a sealing cap located along said centerline adjacent said opening for engagement by said male luer;

a cylindrical shaft located along said centerline between said sealing cap and said piston, said shaft being movable into and out of said neck portion, said shaft and said piston cooperating with each other for automatically and reversibly increasing in size a fluid space located in said cavity when said male luer is connected to said connector and contracting the fluid space in size when said male luer is disconnected;

a chamber positioned in said body isolated from said fluid space, said chamber adapted to expand and contract when said sealing device moves between said closed position and said open position; and a spring positioned in said chamber and engaging said piston for biasing said sealing device into said closed position.

9. The medical valve of claim 8, wherein said sealing cap further comprises a slit.

10. The medical valve of claim 8, wherein the surface of the sealing cap is adapted to be swabable.

11. The medical valve of claim 10, wherein a portion adjacent to said opening of said body comprises one or more screw threads.

12. The medical valve of claim 8, wherein said sealing device further comprises a shoulder.

13. A medical valve adapted to facilitate fluid flow between a first medical implement and a second medical implement, comprising:

a body having a cavity in fluid communication with a second medical implement and an opening adapted to receive a first medical implement, said cavity having a neck portion and a larger diameter main portion, a border between the neck portion and the main portion creating an annular wall; and a sealing mechanism in the cavity movable between a first position in which the sealing mechanism prevents fluid flow through said cavity and a second position in which fluid flow is permitted through said cavity, said sealing mechanism comprising:

a cap for engagement of said first medical implement;

a cylindrical shaft being axially moveable into and out of the neck portion;

a rigid disk shaped piston coupled to the shaft, the piston and the shaft having different diameters to define an annular region to cooperate with the annular wall to create a fluid space, the annular region adapted to move axially away from the annular wall when the sealing mechanism moves into the second position so that the fluid space is increased in size and the annular region is adapted to move axially toward the annular wall when the sealing mechanism moves into the first position so that the fluid space is decreased in size; and an air filled chamber isolated from the fluid space, the chamber having a spring positioned in the chamber and engaging the piston for biasing the sealing mechanism into the closed position.

14. The medical valve of claim 13, wherein an area defined by a radial cross-section of the piston is at least twice as large as an area defined by a radial cross-section of the shaft.

15. The medical valve of claim 14, wherein the area of the piston is at least three times as large as the area of the shaft.

16. The medical valve of claim 13, wherein said cap further comprises a slit.

17. The medical valve of claim 13, wherein the surface of the sealing cap is adapted to be swabable.

18. The medical valve of claim 13, wherein said sealing mechanism further comprises a shoulder for engagement with said annular wall.

* * * * *

UNITED STATES PATENT AND TRADEMARK OFFICE
CERTIFICATE OF CORRECTION

PATENT NO. : 6,932,795 B2
DATED : August 23, 2005
INVENTOR(S) : Lopez et al.

It is certified that error appears in the above-identified patent and that said Letters Patent is hereby corrected as shown below:

Column 7,
Line 38, delete "a" and insert -- an --;

Column 27,
Line 32, after "thereof" add -- . --;

Column 28,
Line 12, delete "patent" and insert -- patient --;
Line 34, after "shaft" delete ":";
Line 55, delete "potion" and insert -- portion --;
Line 57, delete "theads" and insert -- threads --.

Signed and Sealed this

Second Day of May, 2006

JON W. DUDAS
*Director of the United States Patent and Trademark Office*